(12) United States Patent
Tominaga et al.

(10) Patent No.: US 9,583,231 B2
(45) Date of Patent: Feb. 28, 2017

(54) CARBON NANOTUBE COMPOSITE ELECTRODE AND METHOD FOR MANUFACTURING THE SAME

(75) Inventors: Masato Tominaga, Kumamoto (JP);
Shingo Sakamoto, Kumamoto (JP);
Yuichi Fukamichi, Kumamoto (JP);
Ayako Iwaoka, Kumamoto (JP);
Terutaka Hashiguchi, Kumamoto (JP);
Makoto Togami, Kumamoto (JP);
Noriaki Watanabe, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 541 days.

(21) Appl. No.: 14/115,938

(22) PCT Filed: May 10, 2012

(86) PCT No.: PCT/JP2012/061967
§ 371 (c)(1),
(2), (4) Date: Nov. 6, 2013

(87) PCT Pub. No.: WO2012/157506
PCT Pub. Date: Nov. 22, 2012

(65) Prior Publication Data
US 2014/0113127 A1    Apr. 24, 2014

(30) Foreign Application Priority Data

May 13, 2011    (JP) .................................. 2011-108659

(51) Int. Cl.
| | | |
|---|---|---|
| H01B 1/24 | (2006.01) | |
| H01B 1/04 | (2006.01) | |
| H01B 1/18 | (2006.01) | |
| H01L 35/22 | (2006.01) | |
| H01M 4/96 | (2006.01) | |
| H01M 4/583 | (2010.01) | |
| H01L 51/44 | (2006.01) | |
| B82Y 30/00 | (2011.01) | |
| B82Y 40/00 | (2011.01) | |
| C01B 31/02 | (2006.01) | |
| H01B 13/00 | (2006.01) | |
| G01N 27/30 | (2006.01) | |

(52) U.S. Cl.
CPC ............... *H01B 1/24* (2013.01); *B82Y 30/00* (2013.01); *B82Y 40/00* (2013.01); *C01B 31/0233* (2013.01); *H01B 1/04* (2013.01); *H01B 1/18* (2013.01); *H01B 13/0036* (2013.01); *H01L 35/22* (2013.01); *H01L 51/444* (2013.01); *H01M 4/583* (2013.01); *H01M 4/96* (2013.01); *C01B 2202/02* (2013.01); *C01B 2202/34* (2013.01); *C01B 2202/36* (2013.01); *G01N 27/308* (2013.01); *Y02E 10/542* (2013.01); *Y02E 10/549* (2013.01); *Y02P 70/521* (2015.11); *Y10T 428/25* (2015.01)

(58) Field of Classification Search
None
See application file for complete search history.

(56) References Cited

U.S. PATENT DOCUMENTS

| | | | |
|---|---|---|---|
| 2002/0165091 A1 | 11/2002 | Resasco et al. | |
| 2004/0070009 A1 | 4/2004 | Resasco et al. | |
| 2004/0186011 A1 | 9/2004 | Resasco et al. | |
| 2005/0025696 A1 | 2/2005 | Resasco et al. | |
| 2007/0116630 A1 | 5/2007 | Resasco et al. | |
| 2008/0105544 A1* | 5/2008 | Shigematsu ........... B82Y 15/00 204/400 |
| 2008/0107588 A1 | 5/2008 | Resasco et al. | |

FOREIGN PATENT DOCUMENTS

| | | |
|---|---|---|
| CN | 1360558 | 7/2002 |
| CN | 1629628 | 6/2005 |
| JP | 2005-332612 | 12/2005 |
| JP | 2008-64724 | 3/2008 |
| JP | 2009-76568 | 4/2009 |
| JP | 2009-226390 | 10/2009 |

OTHER PUBLICATIONS

International Search Report issued Jul. 17, 2012 in International (PCT) Application No. PCT/JP2012/061967.

* cited by examiner

*Primary Examiner* — Sheeba Ahmed
(74) *Attorney, Agent, or Firm* — Wenderoth, Lind & Ponack, L.L.P.

(57) ABSTRACT

Provided is a carbon nanotube composite electrode having carbon nanotubes which are firmly fixed to an electrode substrate so as to utilize the characteristics of the carbon nanotubes, and having the intrinsic electrode characteristics of carbon nanotubes. The carbon nanotube composite electrode has a surface layer containing a porous oxide material and carbon nanotubes on the surface of the electrode substrate, wherein the carbon nanotubes are generated from the porous oxide material, and at least some of the carbon nanotubes are electrically connected to the electrode substrate. The carbon nanotube composite electrode is firmly fixed to the electrode substrate, and has the intrinsic electrode characteristics of carbon nanotubes, and thus may preferably be used in applications for electrodes and the like in various electronic devices such as electrochemical sensors and batteries.

16 Claims, 25 Drawing Sheets

Au(bare)

Au(CNT)

- - - With oxygen degassed
——— With oxygen aerated

- - - With no glucose
——— With 50 mM glucose

US 9,583,231 B2

CARBON NANOTUBE COMPOSITE ELECTRODE AND METHOD FOR MANUFACTURING THE SAME

CROSS-REFERENCE TO RELATED APPLICATION

The present application is based on the International Application No. PCT/JP2012/061967 which was filed on May 10, 2012 and claims priority under 35 U.S.C. 119 from Japanese Patent Application No. 2011-108659 which was filed on May 13, 2011.

TECHNICAL FIELD

The present invention relates to a carbon nanotube composite electrode and a method for manufacturing the same.

BACKGROUND ART

A carbon nanotube is a tubular substance having a diameter of about 0.4 nm to several tens of nanometers obtained by rolling one layer of graphene sheet (a layer made of a six-membered carbon ring) into a cylinder. The carbon nanotubes are attracting people's attention as an excellent nanomaterial having thermal and chemical stability, mechanical strength, electron conductivity, thermal conductivity, and spectral characteristics that extend up to a near infrared region.

Among the carbon nanotubes (which may hereafter be referred to as "CNT"), there are a single-walled carbon nanotube (SWCNT) made of only one layer of the graphene sheet, a double-walled carbon nanotube (DWCNT) made of two layers of the graphene sheets, and a multi-walled carbon nanotube (MWCNT) made of two or more layers of the graphene sheets.

As an application example of carbon nanotubes, a carbon nanotube composite electrode (CNT composite electrode) in which the carbon nanotubes are fixed onto an electrode substrate is being developed.

For example, Japanese Patent Document 1 (JP-2008-64724 A) discloses a CNT composite electrode provided with CNTs that are grown from a metal catalyst fixed onto an electrode substrate.

By this method, the CNTs are formed directly on the electrode substrate, so that the electron movement between the CNTs and the electrode is easy, and the CNT composite electrode can be used as a highly sensitive sensor. On the other hand, the bonding force between the CNTs and the electrode is insufficient, so that the CNTs are liable to drop off. In particular, when it is necessary that the CNT composite electrode is immersed in water for application as a sensor or the like, there is a problem in that the CNTs are easily desorbed.

Japanese Patent Document 2 (JP-2005-332612 A) discloses a method for manufacturing a CNT composite electrode in which CNTs are immobilized by depositing on an electrode substrate a mixture of fine particles containing a major component of the electrode substrate and CNTs and heating the resultant in oxygen-free atmosphere to turn the fine particles into a coating film.

In this CNT composite electrode, the CNTs are fixed while being interposed between the fine particles containing the major component of the electrode substrate, so that the CNTs are firmly fixed onto the electrode. However, at the time of fixing, the CNT wall surface is damaged by the fine particles containing the major component of the electrode substrate, so that the intrinsic characteristics of the CNTs cannot be sufficiently obtained. Also, this method has a disadvantage in that the amount of CNTs that can be fixed per unit electrode area cannot be made so large.

PRIOR ART DOCUMENTS

Patent Documents

SUMMARY OF THE INVENTION

Under such circumstances, an object of the present invention is to provide a carbon nanotube composite electrode in which carbon nanotubes are firmly fixed to an electrode substrate so as to utilize the characteristics thereof and which has the intrinsic electrode characteristics of carbon nanotubes, as well as a method for manufacturing the same.

As a result of earnest studies carried out in order to solve the aforementioned problems, the present inventors have found out that the following invention meets the aforementioned object, thereby arriving at the present invention.

In other words, the present invention is related to the following aspects.

<1> A carbon nanotube composite electrode having a surface layer containing a porous oxide material and carbon nanotubes on a surface of an electrode substrate, wherein the carbon nanotubes are generated from the porous oxide material, and at least some of the carbon nanotubes are electrically connected to the electrode substrate.

<2> The carbon nanotube composite electrode according to <1>, wherein the porous oxide material is at least one kind selected from the group consisting of zeolite, activated alumina, and mesoporous silica.

<3> The carbon nanotube composite electrode according to <2>, wherein the porous oxide material is zeolite.

<4> The carbon nanotube composite electrode according to any one of <1> to <3>, wherein the electrode substrate is an electrode substrate made of gold (Au) or an electrode substrate plated with gold (Au).

<5> The carbon nanotube composite electrode according to any one of <1> to <4>, wherein some of the carbon nanotubes generated from the porous oxide material are partially embedded in the surface of the electrode substrate.

<6> The carbon nanotube composite electrode according to any one of <1> to <5>, wherein the carbon nanotubes contain carbon nanotubes generated from pores of the porous oxide material.

<7> The carbon nanotube composite electrode according to any one of <1> to <6>, wherein the carbon nanotubes are carbon nanotubes generated from metal catalyst fine particles supported on the porous oxide material.

<8> The carbon nanotube composite electrode according to <7>, wherein the amount of the supported metal fine particles is 0.1 parts by weight or more and 10 parts by weight or less relative to 100 parts by weight of the porous oxide material.

<9> The carbon nanotube composite electrode according to any one of <1> to <8>, wherein 70% or more of the total number of the carbon nanotubes are single-walled carbon nanotubes.

<10> The carbon nanotube composite electrode according to any one of <1> to <9>, wherein the carbon nanotubes are non-oxidized type carbon nanotubes.

<11> The carbon nanotube composite electrode according to any one of <1> to <10>, wherein a metal and/or a semiconductor are firmly immobilized on a wall surface of the carbon nanotubes.

<12> The carbon nanotube composite electrode according to <11>, wherein the metal and/or the semiconductor are fine particles having an average particle size of 100 nm or less.

<13> The carbon nanotube composite electrode according to <12>, wherein 80% or more of the total number of the fine particles have a particle size within a range of 0.5 nm or more and 5 nm or less.

<14> The carbon nanotube composite electrode according to any one of <1> to <13>, wherein a wall surface of the carbon nanotubes is covered with a surface-modifying substance.

<15> The carbon nanotube composite electrode according to <14>, wherein the surface-modifying substance is a surfactant.

<16> The carbon nanotube composite electrode according to any one of <1> to <15>, wherein a tip of at least some of the carbon nanotubes is open-ended.

<17> The carbon nanotube composite electrode according to <16>, which is electrochemically open-ended.

<18> The carbon nanotube composite electrode according to <16> or <17>, wherein the open-ended carbon nanotubes incorporate an incorporated modifying substance.

<19> The carbon nanotube composite electrode according to <18>, wherein the incorporated modifying substance is carotenoid.

<20> An electrochemical sensor having the carbon nanotube composite electrode according to any one of <1> to <19>.

<21> A power-generating device having the carbon nanotube composite electrode according to any one of <1> to <19>.

<22> The power-generating device according to <21>, which is any one kind selected from a dye-sensitized solar cell, a biofuel cell, and a thermoelectric power-generating device.

<23> A power storage device having the carbon nanotube composite electrode according to any one of <1> to <19>.

<24> A carbon nanotube-porous oxide material composite wherein the electrode substrate has been removed from the carbon nanotube composite electrode according to any one of <1> to <19>.

<25> A method for opening an end of a carbon nanotube, including applying an electric potential to the carbon nanotube composite electrode according to any one of <1> to <15> to electrochemically decompose a tip of the carbon nanotube contained in the electrode.

<26> A method for manufacturing a carbon nanotube composite electrode, including the steps of:

(1) forming a coating film, which contains porous oxide particles supporting metal catalyst fine particles thereon or porous oxide particles containing a precursor of metal catalyst fine particles, on an electrode substrate;

(2) forming a porous oxide layer containing the metal catalyst fine particles by heat-treating the electrode substrate on which the coating film has been formed; and (3) generating carbon nanotubes from the metal catalyst fine particles supported on the porous oxide material by heat-treating the electrode substrate on which the porous oxide layer has been formed in non-oxidizing atmosphere containing a carbon-containing compound.

<27> The method for manufacturing a carbon nanotube composite electrode according to <26>, wherein the porous oxide particles have pores having a pore diameter within a range of 0.4 nm or more and 20 nm or less, and the porous oxide particles have a specific surface area of 100 $m^2/g$ or more.

<28> The method for manufacturing a carbon nanotube composite electrode according to <26> or <27>, wherein the porous oxide material is zeolite.

<29> The method for manufacturing a carbon nanotube composite electrode according to any one of <26> to <28>, wherein the porous oxide particles have a particle size of 0.05 µm or more and 10 µm or less.

<30> The method for manufacturing a carbon nanotube composite electrode according to any one of <26> to <29>, wherein the amount of the supported metal fine particles is 0.1 parts by weight or more and 10 parts by weight or less relative to 100 parts by weight of the porous oxide material.

<31> The method for manufacturing a carbon nanotube composite electrode according to any one of <26> to <30>, wherein the metal fine particles have a particle size of 0.5 nm or more and 100 nm or less.

<32> The method for manufacturing a carbon nanotube composite electrode according to any one of <26> to <31>, wherein the metal catalyst fine particles are a CoMo alloy.

<33> The method for manufacturing a carbon nanotube composite electrode according to any one of <26> to <32>, wherein the electrode substrate is an electrode substrate made of gold (Au) or an electrode substrate plated with gold (Au).

<34> The method for manufacturing a carbon nanotube composite electrode according to any one of <26> to <33>, wherein the heat treatment temperature in step (2) is 300° C. or more and 900° C. or less.

<35> The method for manufacturing a carbon nanotube composite electrode according to any one of <26> to <34>, wherein the heat treatment temperature in step (3) is 600° C. or more and 900° C. or less.

<36> The method for manufacturing a carbon nanotube composite electrode according to any one of <26> to <35>, wherein the carbon-containing compound is ethanol.

The advantages obtained by the aforementioned present invention will be described hereinbelow.

According to the present invention, there is provided a carbon nanotube composite electrode in which carbon nanotubes generated from a porous oxide material are firmly fixed to an electrode substrate and which has the intrinsic electrode characteristics of carbon nanotubes. The carbon nanotube composite electrode may be suitably used as an electrode of electrochemical sensors, various power-generating devices, and power storage devices such as batteries.

The above and other objects and advantageous features of the present invention will be made apparent from the following description made with reference to the accompanying drawings, in which reference characters designate the same or similar parts throughout the drawings.

DESCRIPTION OF THE PREFERRED EMBODIMENTS

Figure 1A:
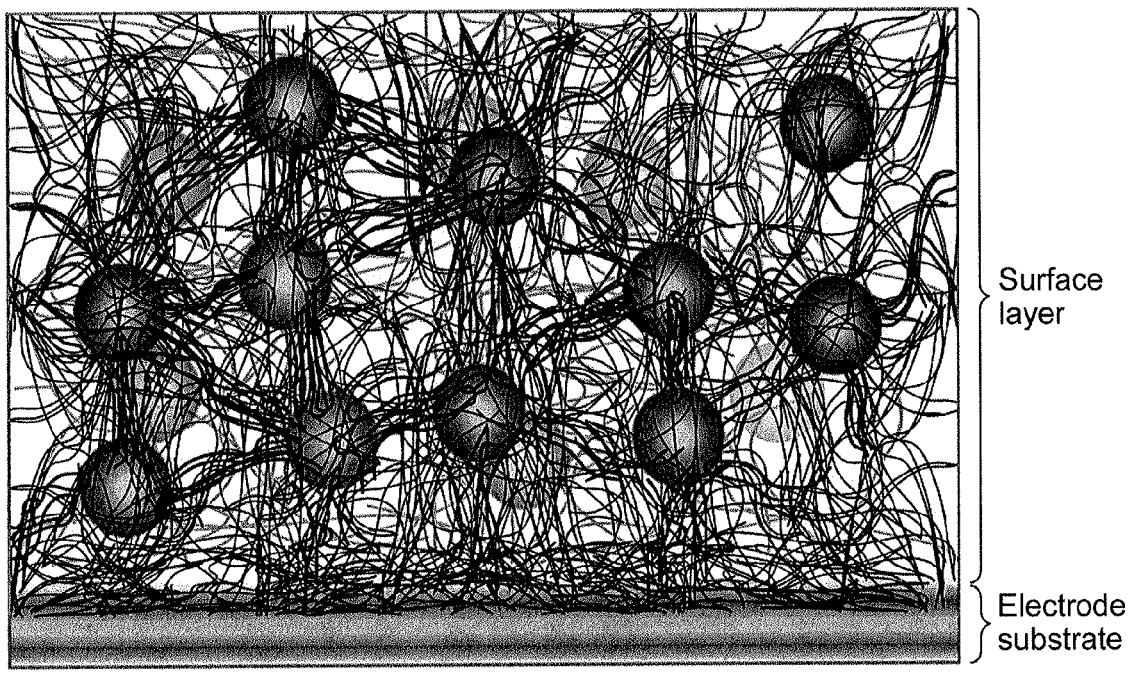
FIG. 1A is a schematic view of a CNT composite electrode containing CNTs generated from pores of a porous oxide material constituting a surface layer, which is one embodiment of a CNT composite electrode of the present invention.

The present invention relates to a carbon nanotube composite electrode (hereafter referred to as a "CNT composite electrode of the present invention") having a surface layer containing a porous oxide material and carbon nanotubes on a surface of an electrode substrate, wherein the carbon nanotubes are generated from the porous oxide material, and at least some of the carbon nanotubes are electrically connected to the electrode substrate.

In the CNT composite electrode of the present invention, numerous CNTs generated from the porous oxide material are in contact with one another and at least some of the CNTs are electrically connected to the electrode substrate. Therefore, the CNT composite electrode of the present invention sufficiently has the intrinsic electrode characteristics of the CNTs and is excellent in electric conductivity of the electrode as a whole.

Hereafter, the constituent elements of the CNT composite electrode of the present invention will be described in detail.

"1. Electrode Substrate"

In the CNT composite electrode of the present invention, the electrode substrate is not particularly limited as long as it has electric conductivity. Specifically, the electrode substrate may be made, for example, of a metal such as gold (Au), silver (Ag), platinum (Pt), copper (Cu), iron (Fe), nickel (Ni), cobalt (Co), molybdenum (Mo), or titanium (Ti), or an alloy thereof, or one in which a coating film made of the aforementioned metal, an alloy thereof, or an electrically conductive oxide is formed on a surface of a base material of glass or ceramic. Here, the electrically conductive oxide (including a semiconductor) may be, for example, tin-doped indium oxide (ITO), tin oxide ($SnO_2$), zinc oxide (ZnO), titanium oxide ($TiO_2$), or the like.

Here, as will be described later, heating is carried out at the time of generating CNTs, so that the electrically conductive oxide preferably has heat resistance at a temperature of 600° C. or more.

Among the aforementioned electrode substrates, a metal such as gold (Au), platinum (Pt), copper (Cu), nickel (Ni), molybdenum (Mo), or titanium (Ti), or an alloy thereof is preferably used because of having higher heat resistance and because the surface layer of the porous oxide material can be formed more easily. Here, as will be described later, in the manufacturing method of the present invention, the CNTs are generated from the porous oxide layer formed on the electrode substrate. When a metal or an alloy thereof is used as the electrode substrate, there is a tendency such that the metal is softened under the later-mentioned conditions of generating the CNTs, so that the generated CNTs go into the electrode substrate by interaction between the carbon on the CNT surface and the metal atoms, thereby resulting in a form in which some of the CNTs among the CNTs are partially embedded in the surface of the electrode substrate. Here, there are cases where the CNTs are generated under reduced pressure; when the CNTs are generated under reduced pressure, the melting point or the softening temperature of the metal used in the electrode substrate tends to decrease, so that the embedding of the CNTs is more liable to occur. This results in an advantage such that the CNTs are firmly fixed to the electrode substrate, and also the electron transfer property between the CNTs and the electrode substrate is improved. Gold (Au) is one of the suitable electrode substrate materials because of having high chemical stability and easily provoking embedding of the CNTs by being softened under the conditions of generating the CNTs.

Here, the surface of the electrode substrate may be covered with plating. For this reason, one in which a less expensive metal such as copper (Cu) or iron (Fe) is used as a base material and the surface thereof is plated with an expensive metal such as gold (Au) or platinum (Pt), for example, may be used as the electrode substrate. Alternatively, one in which a non-electrically-conductive material having excellent heat resistance such as glass or ceramic is plated with a metal may be used as the electrode substrate. As described above, gold (Au) is preferable as a material for metal plating because of having high chemical stability.

The shape of the electrode substrate may be any of a flat plate shape, a net shape, and a columnar shape. Here, from the viewpoint of enhancing the property of fixing to the surface layer, the electrode substrate preferably has a cylindrical shape. Alternatively, in order to increase the electrode surface area, the electrode substrate preferably has a net shape. Here, the size of the electrode substrate is not particularly limited and is suitably selected in consideration of the purpose of use.

"2. Surface Layer"

The surface layer in the CNT composite electrode of the present invention is constituted of a porous oxide material and CNTs. The CNTs are generated on the porous oxide material, and at least some of the CNTs are electrically connected to the electrode substrate. The surface layer is formed on the whole of or on a part of the surface of the electrode substrate in accordance with the purpose thereof. The thickness thereof can be suitably determined in accordance with the purpose of use; however, the thickness is generally about 0.1 to 100 µm.

Hereafter, the porous oxide material and the CNTs constituting the surface layer will be described.

(i) Porous Oxide Material

The porous oxide material is an oxide material having numerous pores of a nano-order level (generally 100 nm or less). In the CNT composite electrode of the present invention, the porous oxide material is fixed to the surface of the electrode substrate as a porous layer through which gas or a liquid can pass.

The pores are preferably mesopores of 2 to 50 nm; however, the porous oxide material may have micropores having a diameter less than 2 nm or macropores having a diameter exceeding 50 nm.

From the viewpoint of obtaining more homogeneous CNTs, the porous oxide material preferably has pores having a pore diameter within a range of 0.4 nm or more and 20 nm or less.

The porous oxide material may be one having heat resistance at a processing temperature at the time of forming the CNTs (600° C. or more). The porous oxide material may be, for example, silica ($SiO_2$) such as mesoporous silica, alumina ($Al_2O_3$) such as activated alumina, magnesia (MgO), titanic ($TiO_2$), aluminosilicate such as zeolite, or a composite oxide of these. These may be used either as one kind or as a combination of two or more kinds.

Among these, activated alumina, mesoporous silica, and zeolite are suitable.

These porous oxide materials can be formed, for example, by heating a source material precursor (for example, aluminum alkoxide or alkoxysilane) and a combustible or thermally decomposable organic compound for forming pores together with a template material.

Here, as will be described in detail in the later-mentioned method for manufacturing a CNT composite electrode of the present invention, the porous oxide layer can be obtained by heat-treating a coating film containing particles of a porous oxide material. The pore diameter and the specific surface area of the porous oxide material suitable as a source material will also be described later in the method for manufacturing a CNT composite electrode of the present invention.

Among these, zeolite is a preferable porous oxide material because of having high heat resistance and a large specific surface area.

Zeolite is a generic name for crystalline aluminosilicates having fine pores of about 0.4 nm to 2 nm in the crystal and has a three-dimensional network structure in which a Si—O tetrahedron and an Al—O tetrahedron have an O atom of an apex in common. The zeolite may be, for example, ZSM-5-type zeolite, faujasite-type zeolite, mordenite-type zeolite, L-type zeolite, A-type zeolite, X-type zeolite, Y-type zeolite, or the like. Among these, Y-type zeolite having high heat resistance is preferable.

(ii) Carbon Nanotube (CNT)

The CNTs formed on the porous oxide material in the surface layer can transfer electrons to and from the electrode substrate because at least a part of the CNTs are electrically connected to the electrode substrate.

The CNTs may contain single-walled CNTs, multi-walled CNTs, and a mixture of these. In particular, it is preferable that 70% or more of the total number of the CNTs are single-walled CNTs. Here, the ratio of the single-walled CNTs is preferably 80% or more, more preferably 90% or more, and particularly preferably 95% or more (including 100%).

The single-walled CNTs have a higher quality than multi-walled CNTs. Therefore, when the ratio of the single-walled CNTs is more than or equal to the aforementioned ratio, it gives an advantage such that the inherent property of the CNTs can be effectively utilized. Here, the ratio of the single-walled CNTs can be determined by counting the number of single-walled CNTs in randomly selected 100 CNTs in TEM.

The length and the thickness of the CNTs can be confirmed by a scanning electron microscope (SEM) or a transmission electron microscope (TEM). Here, a plurality of CNTs may grow in a bundle form instead of growing singly one by one. The CNTs in a bundle form can be observed by a SEM.

The length and the thickness of the CNTs formed on the porous oxide material are not particularly limited; however, the total length is generally about 0.1 to 10000 µm, preferably 1 µm to 1000 µm, and the diameter is generally about 0.5 to 100 nm, preferably 0.5 nm to 2 nm.

The density of the CNTs in the surface layer may be of such a degree that the formed CNTs are in contact with one another and, as a whole, have sufficient electric conductivity to be capable of transferring electrons to and from the electrode. In the CNT composite electrode of the present invention, the density of the CNTs per unit surface area of the porous oxide material is generally $1\times10^8/cm^2$ to $1\times10^{14}/cm^2$, preferably $1\times10^{11}/cm^2$ to $1\times10^{13}/cm^2$.

The distance between the CNTs (in the case of CNTs in a bundle form, the distance between the bundled CNTs) is generally 0.2 to 1000 nm, preferably 1 nm to 100 nm.

Here, it is preferable that the CNTs contain CNTs generated from the pores of the porous oxide material constituting the surface layer. In particular, the ratio of the CNTs generated from the pores is preferably 50% or more of the total CNTs, more preferably 80% or more of the total CNTs.

Figure 1B:
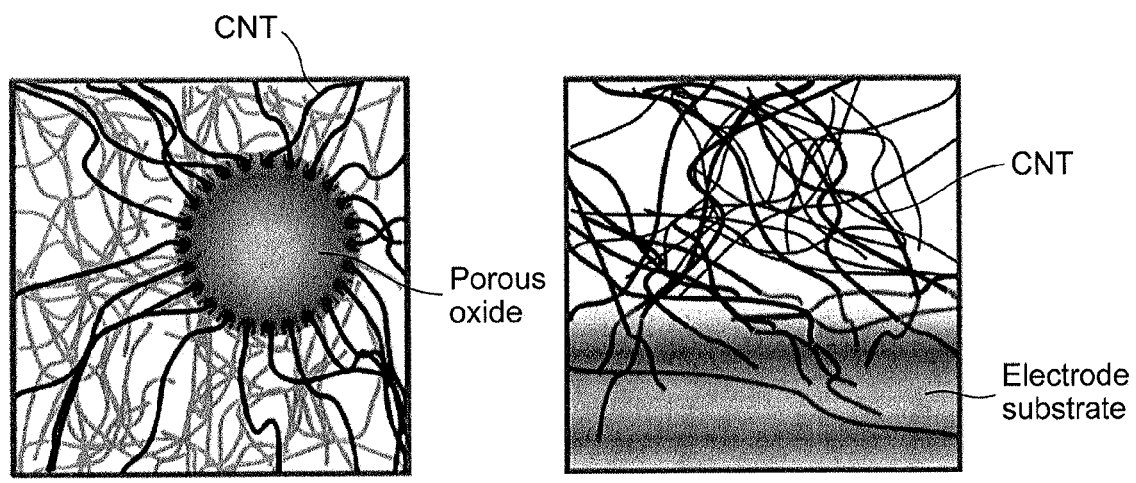
FIG. 1B is an enlarged schematic view of a surface layer part and an enlarged schematic view of an electrode substrate part in FIG. 1A.

As one example of a suitable form of the CNT composite electrode of the present invention, FIG. 1A shows a schematic view of a CNT composite electrode containing CNTs generated from the pores of the porous oxide material constituting the surface layer, and FIG. 1B shows an enlarged schematic view of the surface layer part and an enlarged schematic view of the electrode substrate part. Here, in these schematic views, a state is shown in which the particles of the porous oxide material are separated from one another by the stress accompanying the growth of the CNTs; however, there may be a state in which the particles of the porous oxide material are in a bulk state without being separated from one another as before the growth of the CNTs.

FIGS. 1A and 1B also show an appearance of the interface between the electrode substrate and the surface layer; however, as described above, there may be a case where the grown CNTs are partially embedded in the surface of the electrode substrate.

As will be described later in the method for manufacturing a CNT composite electrode of the present invention, the CNTs may be grown, for example, from metal catalyst fine particles supported on a porous oxide material. In this case, the amount of the supported metal fine particles is preferably 0.1 parts by weight or more and 10 parts by weight or less, more preferably 0.2 parts by weight or more and 5 parts by weight or less, relative to 100 parts by weight of the porous oxide material in view of the yield. Here, the kind and size of the metal catalyst fine particles and a specific method for synthesizing CNTs will be described later in the method for manufacturing a CNT composite electrode of the present invention.

In addition, such metal catalyst fine particles may be dissolved and removed by using a suitable chemical agent after the CNTs are formed.

It is preferable that the carbon nanotubes contain carbon nanotubes generated from the pores of the porous oxide material constituting the surface layer. The diameter of such CNTs is restricted to the size of the pores of the porous oxide material. For this reason, when zeolite having fine pores of about 0.4 nm to 2 nm in the crystal, for example, is used as the porous oxide material, CNTs whose diameter is restricted by the fine pores can be obtained.

Here, in order to obtain CNTs generated from the pores of the porous oxide material, the CNTs may be grown under suitable conditions after the metal catalyst fine particles are allowed to be supported in the pores of the porous oxide material.

The CNT in the CNT composite electrode of the present invention may be either a "non-oxidized type CNT" whose wall surface is not oxidized or an "oxidized type CNT" whose wall surface is oxidized, and the different CNTs may be used depending on the purpose.

In other words, in the case of making use of the inherent property of the CNT surface or in the case where high electric conductivity is needed such as for the purpose of an electrode for a solar cell or an electrochemical sensor electrode, the CNT is preferably a non-oxidized type CNT having fewer functional groups on the wall surface.

On the other hand, in the synthesis reaction using the functional groups on the CNT surface or in the case where high electric conductivity is not needed such as for the purpose of a drug delivery system or for the purpose of developing a functional material of photofunctional molecule modification or the like, an oxidized type CNT can be used as well.

Here, a "non-oxidized type CNT" can be obtained as a CNT immediately after the synthesis. The non-oxidized type CNT is hardly oxidized even when stored in air; however, contamination by oily components is liable to adhere, so that the non-oxidized type CNT is preferably stored in non-oxidizing atmosphere (including a liquid) immediately after the synthesis.

The "oxidized type CNT" can be obtained, for example, by subjecting a non-oxidized type CNT to a plasma treatment, a UV-ozone treatment, a treatment at a high temperature (about 300 to 600° C.), a treatment with an oxidizing reagent such as hydrogen peroxide, or an electrochemical oxidation treatment.

In addition, among the CNTs in the CNT composite electrode of the present invention, some of the CNTs may have an open end.

As a method for opening an end of a CNT, there are, for example, a method of heating at 350° C. to 600° C. in air or performing plasma-etching or using a chemical agent such as hydrochloric acid, sulfuric acid, nitric acid, phosphoric acid, hydrogen peroxide, or mixed acid to dissolve a tip part of the CNT in the CNT composite electrode, and a method of opening the end by applying an electric potential to the CNT composite electrode to electrochemically decompose the tip of the CNT contained in the electrode. Here, by the method of dissolving the tip part of the CNT by using a chemical agent, not only the tip part of the CNT but also the side wall part thereof is inevitably damaged. However, the method of electrochemically opening the tip part of the CNT composite electrode gives an advantage in that only the tip can be selectively decomposed by suitably selecting the electric potential conditions.

The range of applied electric potential suitable for opening an end of a CNT depends on the solution pH, coexistent ion species, and the like; however, a suitable range of applied electric potential under the conditions of a 0.1 M phosphate buffer solution of pH 7 is 0.8 to 1.2 V, more preferably 0.9 to 1.1 V, in terms of Ag/AgCl (saturated KCl). Here, Ag/AgCl (saturated KCl) may in some cases be referred to as Ag/AgCl.

"3. Modification of CNT Composite Electrode"

(3-1. Adhesion of Metal and/or Semiconductor to CNT Wall Surface)

In the CNT composite electrode of the present invention, a metal and/or a semiconductor may be allowed to adhere onto the wall surface (outer wall surface) of the CNT, whereby a property (for example, a catalytic action) derived from the adhered metal and/or semiconductor can be imparted to the CNT.

The form of the metal and/or the semiconductor allowed to adhere onto the CNT wall surface is determined in consideration of the purpose of use, ease of forming, and the like. The metal and/or the semiconductor may be allowed to adhere onto the CNT wall surface as fine particles, or may be allowed to adhere as a film so as to cover the CNT wall surface.

Here, when the metal and/or the semiconductor are allowed to adhere as fine particles, the metal and/or the semiconductor are preferably metal fine particles and/or semiconductor fine particles having an average particle size of 100 nm or less, more preferably those having an average particle size of 20 nm or less.

In particular, because synthesis of single-walled CNTs having a high quality can be promoted by suppressing the generation of multi-walled CNTs, it is preferable that 80% or more, more preferably 90% or more of the total number of the fine particles have a particle size within a range of 0.5 to 5 nm.

Here, the average particle size of the fine particles is a value obtained by randomly extracting 100 particles by a scanning electron microscope (SEM) or a transmission electron microscope (TEM), measuring the particle size (diameter) for each particle, and calculating the average value of the particle sizes of the 100 particles. When the shape of the fine particles is other than a spherical shape, the length in the direction indicating the maximum length in the particle is regarded as the particle size thereof.

A metal suitable for such fine particles may be, for example, gold (Au), silver (Ag), copper (Cu), platinum (Pt), palladium (Pd), or the like.

In addition, the metal semiconductor may be, for example, titanium oxide ($TiO_2$), tin oxide ($SnO_2$), zinc oxide (ZnO), or the like.

As a method for allowing the fine particles to be supported on the CNT, production may be carried out from the metal precursor or metal semiconductor precursor by any production method. The precursor of metal or metal semiconductor may be, for example, an oxide, a hydroxide, a halide, a nitrate, a sulfate, a carbonate, an oxalate, an acetate, a metal carbonyl, or the like.

(3-2. Covering of CNT Wall Surface with Surface-Modifying Substance)

The wall surface of CNTs may be covered with a surface-modifying substance. Here, a "surface-modifying substance" refers to a substance that is adsorbed onto the CNT wall surface to cover the surface.

Examples of the surface-modifying substance include surfactants, lipids, amino acids and polymer-form substances thereof (including proteins and enzymes), other CNT-adsorbing polymers, and the like.

In the case of surface modification that is intended for weak interaction with a CNT wall surface, surfactants and lipids are preferably used.

As the surfactants and lipids, for example, sodium lauryl sulfate, sodium dodecylbenzenesulfate, sodium deoxycholate, sodium cholate, hexadecyltrimethylammonium bromide, phosphatidylcholine, ditetradecyl phosphate, N,N-didodecyl-ω-(gluconoamide)-hexamide, and the like can be used.

Examples of the polymer include polyparaphenylenevinylene derivatives and conjugate polymers, pyrene polymers, carboxymethyl cellulose, chitosan, gelatin, polystyrene-polyacrylic acid block polymers, polyimides, polybenzimidazoles, and the like.

(3-3. Modification by a to-be-Incorporated Modifying Substance into CNT Inside)

In addition, in the CNT composite electrode of the present invention, in the case of a CNT composite electrode containing open-ended CNTs described above, a to-be-incorporated modifying substance can be incorporated into the inside of CNTs. By incorporating a to-be-incorporated modifying substance into the CNTs, a new function can be imparted to the CNT composite electrode.

Here, a to-be-incorporated modifying substance refers to a modifying substance that can go into a carbon nanotube and is specifically a molecule or an atom having a size smaller than the inner diameter of the carbon nanotube, an assembly of a single kind of these, or a composite assembly of these.

The to-be-incorporated modifying substance is selected in consideration of various conditions including the intended function, the diameter and length of the CNT to incorporate the modifying substance, and the like. The to-be-incorporated modifying substance may be, for example, metal or metal compound fine particles, various pigments, carotenoid, fluorescent substances, and the like having a size smaller than the inner diameter of the CNT.

For example, in the CNT composite electrode of the present invention, metallic CNTs and semiconductive CNTs are mixedly present in many cases. When a substance having an electron-donating property of donating electrons to the CNT is incorporated into the CNT as a to-be-incorporated modifying substance, the semiconductive CNTs are converted into metallic CNTs, whereby the CNT composite electrode can be formed into a metallic CNT composite electrode as a whole of the CNTs. Alternatively, when a substance having an electron-attracting property of attracting electrons from the CNT is incorporated into the CNTs as a to-be-incorporated modifying substance, it can be expected that the metallic CNTs are converted into semiconductive CNTs, and the CNT composite electrode can be expected to be formed into a semiconductive CNT composite electrode as a whole.

"4. Application Example of CNT Composite Electrode"

The CNT composite electrode of the present invention has a large effective surface area as a CNT, and the inherent characteristics of the CNT can be effectively utilized, so that the CNT composite electrode of the present invention can be widely applied as an electrode for various devices.

In particular, the CNT composite electrode can be suitably used in electrochemical sensors (including enzyme sensors), dye-sensitized solar batteries, fuel cells (including biofuel cells of enzyme reaction type), power-generating devices such as thermoelectric power-generating devices, primary batteries, secondary batteries, power storage devices such as capacitors, and the like.

Here, the CNT composite electrode may be used after the CNT surface is subjected to an oxidation treatment or is modified with a metal, a semiconductor, or a surface-modifying substance as described above, in accordance with the intended use of various devices.

In addition, when the CNT composite electrode of the present invention is used for enzyme electrode use in which an enzyme is immobilized on an electrode that is used in an enzyme sensor or an enzyme reaction biofuel cell, not only a sufficient amount of the enzyme can be sustained on the surface of the electrode but also the substrate thereof is sufficiently diffused into the inside of the CNT composite electrode because the CNT composite electrode of the present invention has a structure such that the CNTs are moderately extended into the inside of the surface layer. Further, the electrode can perform electron transfer between the CNTs in the upper part and in the inside of the surface layer and the enzyme, so that a more highly sensitive enzyme sensor and a biofuel cell using an enzymatic reaction and having a high output can be realized. Here, for these purposes, a moderately oxidized type CNT composite electrode with enhanced affinity with an enzyme is suitably used in many cases.

In addition, in the synthesis of single-walled carbon nanotubes, semiconductive carbon nanotubes are inevitably mingled by the technique of the state of the art. However, by the to-be-incorporated modifying substance into the inside of the CNTs as described above, a composite CNT electrode which is metallic or semiconductive as a whole can be fabricated. In other words, a single-walled carbon nanotube with an altered electron structure can be fabricated. Because semiconductive ones have an electron transfer resistance, the presence thereof is not preferable when they are used as an electrode for a fuelcell. In particular, in large-scale power generation, this leads to a large loss of the electric current. By using a modification-incorporating composite CNT electrode that enhances the metallic property of the CNTs, a carbon nanotube composite electrode being excellent in electric conductivity characteristics can be fabricated, and an improvement in the output of fuel cell can be expected. By using a modification-incorporating CNT composite electrode that enhances the semiconductive property of the CNTs, fabrication of a sensitized solar cell using nanotubes themselves as a sensitizer can be expected.

In addition, the CNT composite electrode of the present invention has a structure such that a surface layer made of a porous oxide material and CNTs is formed on an electrode substrate; however, the CNT composite electrode can also be used as a CNT-porous oxide composite made of the CNTs and the porous oxide material by eliminating the electrode substrate from this composite electrode.

The CNT-porous oxide composite without having an electrode substrate can be used, for example, for usages such as a frame electrode of a gas diffusion electrode, a separator of a fuelcell, a separation column, a reaction column, a detection column, and a separation filter.

The method for eliminating the electrode substrate from the CNT composite electrode may be, for example, a method of mechanically stripping the surface layer made of the CNTs and the porous oxide material off, a method of dissolving the electrode substrate in a suitable chemical agent, a method of electrochemically dissolving the electrode substrate, or the like.

"5. Method for Manufacturing CNT Composite Electrode"

The method for manufacturing a CNT composite electrode described above is not particularly limited; however, a manufacturing method described below (hereafter referred to as a "method for manufacturing a CNT composite electrode of the present invention") is suitable because the CNT composite electrode can be manufactured with good reproducibility by a comparatively easy method.

Hereafter, the method for manufacturing a CNT composite electrode of the present invention will be described.

The method for manufacturing a CNT composite electrode of the present invention is characterized by including the steps of:

(1) forming a coating film, which contains porous oxide particles supporting metal catalyst fine particles thereon or porous oxide particles containing a precursor of metal catalyst fine particles, on an electrode substrate;

(2) forming a porous oxide layer containing the metal catalyst fine particles by heat-treating the electrode substrate on which the coating film has been formed; and (3) generating carbon nanotubes from the metal catalyst fine particles supported on the porous oxide by heat-treating the electrode substrate on which the porous oxide layer has been formed in non-oxidizing atmosphere containing a carbon-containing compound. Here, steps (2) and (3) may be carried out simultaneously.

Hereafter, each of the steps will be described in detail

<Step (1)>

Step (1) is a step of forming a coating film, which contains porous oxide particles supporting metal catalyst fine particles thereon or porous oxide particles containing a precursor of metal catalyst fine particles, on an electrode substrate. Here, the details of the electrode substrate are as described above, so that a detailed description thereof will be omitted here.

The porous oxide particles constituting a source material of the porous oxide layer are particles made of the porous oxide material described above, and the form thereof is not particularly limited, so that the porous oxide particles may have a form of primary particles, secondary particles obtained by agglomeration of these, or further a particle sol synthesized from a precursor.

In addition, the porous oxide particles may contain components (for example, solvents or dispersants) other than the porous oxide material as long as the effect of the present invention is not undermined. Here, the components other than the porous oxide material can be generally removed by a heat treatment in step (2).

The porous oxide particles have micropores having a diameter of less than 2 nm and so-called mesopores having a diameter of 2 to 50 nm as pores. Alternatively, the porous oxide particles may have macropores having a diameter exceeding 50 nm.

From the viewpoint of forming homogeneous CNTs to enhance the fixing force of the CNTs, it is preferable that the porous oxide material mainly has pores having a diameter of 20 nm or less.

A porous oxide material having numerous pores can easily form CNTs having a diameter that accords to the pore diameter because the pores play a role of a guide for CNT growth.

When CNTs are directly grown from a metal catalyst supported on a porous oxide material, it gives an advantage in that the adhesion property between the metal catalyst fine particles and the porous oxide material is improved, and also the adhesion property between the CNTs grown from the metal catalyst fine particles and the porous oxide material is improved by allowing the metal catalyst fine particles to be supported within the pores. For this reason, it is preferable that the metal catalyst fine particles are supported within the pores of the porous oxide material. A method of allowing the metal catalyst fine particles to be supported within the pores of the porous oxide material will be described later.

From the viewpoint of obtaining more homogeneous CNTs, the porous oxide material preferably has pores having a pore diameter within a range of 0.4 nm or more and 20 nm or less.

Here, the generation of single-walled CNTs and multi-walled CNTs depends on the pore diameter of the porous oxide material. Therefore, in order to form single-walled CNTs or multi-walled CNTs selectively, a porous oxide material having a pore diameter within a specific range that is suitable for generation of each kind of CNTs should be used. In addition, the generated CNTs also depend on the particle size of the metal catalyst fine particles, so that the metal catalyst fine particles are preferably metal catalyst fine particles having a particle size that can be supported within the pores of the porous oxide material.

In the case of selectively synthesizing the single-walled CNTs, a porous oxide material having pores with a pore diameter of 0.4 nm to 2 nm is preferable among the porous oxide materials. On the other hand, in order to increase the ratio of the multi-walled CNTs, a porous oxide material having a larger pore diameter should be used.

The specific surface area in the porous oxide particles is generally 10 $m^2/g$ or more, and is preferably 100 $m^2/g$ or more from the viewpoint of sufficiently supporting the metal catalyst and forming the CNTs at a high density.

Here, the upper limit of the specific surface area in the porous oxide particles is not limited as long as the upper limit is within a range such that the mechanical strength thereof can be maintained. The upper limit is generally 1200 $m^2/g$ or less though depending on the kind of the porous oxide material thereof.

Here, the specific surface area and pore diameter (diameter) distribution in the porous oxide material can be determined using the BET method by nitrogen adsorption.

From the viewpoint of synthesizing homogeneous CNTs at a high density, it is preferable that the porous oxide particles have pores having a pore diameter within a range of 0.4 nm or more and 20 nm or less, and the specific surface area of the porous oxide particles is 100 $m^2/g$ or more.

In particular, from the viewpoint of forming single-walled CNTs at a high density, it is preferable that the porous oxide particles have pores having a pore diameter within a range of 0.4 nm or more and 2 nm or less, and the specific surface area of the porous oxide particles is 100 $m^2/g$ or more.

The particle size of the porous oxide particles is selected within a range such that the coating film in step (1) and the porous oxide layer after the heat treatment in step (2) can be homogeneously formed. The specific particle size thereof, though depending on the kind of the porous oxide material, is generally about 0.01 to 100 µm in terms of average particle size. The CNTs are formed on the porous oxide particle surface. When the particle size of the porous oxide particles is too large, the density of the CNTs will be low. Therefore, the average particle size of the porous oxide particles is preferably 0.02 to 10 µm, more preferably 0.05 to 1 µm.

Here, with respect to the average particle size of the porous oxide particles, the average particle size of the fine particles is a value obtained by randomly extracting 100 particles by a scanning electron microscope (SEM), measuring the particle size (diameter) for each particle, and calculating the average value of the particle sizes of the 100 particles. When the shape of the porous oxide particles is other than a spherical shape, the length in the direction indicating the maximum length in the particle is regarded as the particle size thereof.

As described above, the porous oxide material constituting the porous oxide particles may be, for example, silica ($SiO_2$) such as mesoporous silica, alumina ($Al_2O_3$) such as activated alumina, magnesia (MgO), titanic ($TiO_2$), aluminosilicic acid such as zeolite, or a composite oxide of these. These may be used either as one kind or as a combination of two or more kinds.

Among these, activated alumina, mesoporous silica, and zeolite are preferable, and zeolite is especially preferable. Here, the details of zeolite are as described above.

The metal catalyst in the metal catalyst fine particles may be any one as long as the metal catalyst has a catalytic action for forming graphene, so that it is possible to use a metal made of a transition metal element of Group IV to Group XI such as Co, Fe, Ni, Mo, W, Mn, Ti, V, Cr, Nb, Ru, Pd, Rh, Ag, Au, Cu, or Ir, or an alloy thereof, or further a metal compound thereof (for example, a metal oxide or a metal boride). An alloy or a mixture of two or more kinds of these can be used as well.

The precursor of the metal catalyst fine particles may be any one as long as the precursor is soluble or dispersible in the solvent of a coating liquid described later and is decomposed by a heat treatment, and examples thereof include hydroxides, halides, nitrates, sulfates, carbonates, oxalates, acetates, metal carbonyls, and others.

Among these, a CoMo alloy which is an alloy of Co and Mo is suitably used because of having a high catalyst activity particularly for generating CNTs and because carbon byproducts other than the CNTs are less likely to be generated. Here, such metal catalyst fine particles may be removed by using a suitable chemical agent to dissolve the metal catalyst fine particles after the CNTs are formed.

In addition, the particle size of the metal catalyst fine particles is a factor that determines the diameter of the CNTs that are grown and formed with the metal catalyst fine particles serving as a nucleus. For this reason, the particle size can be suitably set in accordance with the diameter of the CNTs intended to be formed; however, in order to form single-walled CNTs, the average particle size of the metal catalyst fine particles is preferably 0.5 nm or more and 100 nm or less, and especially preferably 0.5 nm or more and 10 nm or less. Here, the average particle size of the metal catalyst fine particles is a value obtained by randomly extracting 100 particles by a transmission electron microscope (TEM), measuring the particle size (diameter) for each particle, and calculating the average value of the particle sizes of the 100 particles. When the shape of the fine particles is other than a spherical shape, the length in the direction indicating the maximum length in the particle is regarded as the particle size thereof.

As a method for forming the coating film, there is a method of coating a suspension (coating liquid in a slurry form) containing porous oxide particles on which metal catalyst fine particles are supported or a suspension (coating liquid in a slurry form) containing a precursor of metal catalyst fine particles and porous oxide particles onto an electrode substrate, followed by drying.

As a method of coating the suspension, a conventionally known coating method such as the brush-coating method, the dip-coating method, the spin-coating method, or the spray-coating method may be suitably selected in accordance with the shape of the electrode substrate.

In the case of an electrode substrate having a cylindrical shape, the dip-coating method may be mentioned as an example of a suitable coating method.

In the case of using a suspension containing porous oxide particles on which metal catalyst fine particles are supported, various conventionally known production methods that allow metal catalysts to be supported on supports can be suitably used as a method for allowing the metal catalyst fine particles to be supported on the porous oxide particles. There are a method of supporting by allowing a metal catalyst having a particulate form adjusted in advance to adhere onto porous oxide particles and firing the resultant, a method of dispersing porous oxide particles in a solution containing a precursor of a metal catalyst to allow the precursor of the metal catalyst to be adsorbed onto the porous oxide particles and thereafter drying the particles and performing a heat treatment to thermally decompose the precursor of the metal catalyst to support as the metal catalyst fine particles, and the like. In particular, the latter method using a solution is suitable because the metal catalyst fine particles can be supported conveniently and uniformly on the porous oxide particles.

Here, in the case of supporting the precursor of the metal catalyst by thermal decomposition thereof, the heat treatment in the later-mentioned step (2) may be used.

In other words, first, a suspension containing a precursor of metal catalyst fine particles and porous oxide particles is used as a coating liquid and dried after being coated onto an electrode substrate to form a coating film containing the porous oxide particles made to contain the precursor of the metal catalyst fine particles and thereafter a heat treatment is carried out in step (2) to form a porous oxide layer containing the metal catalyst fine particles. This method gives an advantage in that generation of the metal catalyst fine particles and formation of the porous oxide layer by firing the porous oxide particles can be carried out in one step.

The suspension for forming the coating film can be obtained by dispersing the porous oxide particles on which the metal catalyst fine particles are supported or the precursor of the metal catalyst fine particles and the porous oxide particles.

The solvent is not particularly limited as long as the solvent can disperse the porous oxide particles, and examples thereof include water, an organic solvent, and a mixture liquid of water and an organic solvent. As the organic solvent, alcohols such as methanol and ethanol, ketones such as methyl ethyl ketone, acetone, and acetylacetone, hydrocarbons such as hexane and cyclohexane, and others are used.

The concentration of the porous oxide particles in the suspension may be within a range such that a uniform coating film can be formed and is generally 1 to 90 wt %, preferably 30 to 70 wt %.

The amount of the supported metal fine particles is preferably 0.1 parts by weight or more and 10 parts by weight or less, more preferably 0.2 parts by weight or more and 5 parts by weight or less, relative to 100 parts by weight of the porous oxide material as a loading amount.

Here, when a suspension containing a precursor of metal catalyst fine particles and porous oxide particles is used as the coating liquid, this amount of supporting is a value as converted in terms of metal catalyst fine particles generated after thermal decomposition of the precursor of the metal catalyst fine particles in step (2).

The suspension is coated onto an electrode substrate and dried to form a coating film containing porous oxide particles on the surface of the electrode substrate.

The method of drying the formed coating film may be, for example, a method of vacuum drying, natural drying, spray drying, or the like. According to circumstances, the coating film may be dried in the heat treatment step of step (2) without being subjected to a special drying step.

By this drying step, the solvent and volatile unreacted substances remaining on the coating film can be removed. Here, the later-mentioned temperature raising process accompanying step (2) may be used commonly as the drying step instead of providing a special drying step.

<Step (2)>

Step (2) is a step of forming a porous oxide layer by heat-treating the electrode substrate on which the coating film has been formed in step (1).

By performing the heat treatment in step (2), the porous oxide particles contained in the coating film are sintered to form a porous oxide layer firmly fixed onto the electrode substrate. Here, when the coating film is made of porous oxide particles containing a precursor of metal catalyst fine particles obtained by drying a suspension containing the precursor of the metal catalyst fine particles and the porous oxide particles, the precursor is thermally decomposed by the heat treatment in this step to form the metal catalyst fine particles.

The heat treatment temperature is determined in consideration of the sinterability of the porous oxide particles and the heat resistance of the electrode substrate and is generally 200° C. to 1000° C., preferably 300° C. to 900° C. The heat treatment time is determined within a range such that the porous oxide layer is sufficiently sintered at the aforementioned heat treatment temperature and is generally about 1 to 30 minutes.

When the temperature is too low, there may be cases where the adhesive property of the porous oxide layer onto the electrode substrate is insufficient. When the temperature is too high, sintering of the porous oxide particles proceeds too much to make the porous oxide layer too dense, thereby easily causing problems such as decrease in the gas permeation property and deactivation or agglomeration of the metal catalyst fine particles supported on the porous oxide particles.

Here, the later-mentioned temperature raising step in step (3) may be used commonly as the heat treatment step of step (2).

The atmosphere of heat treatment is suitably selected from among an oxidizing atmosphere containing oxygen such as air, inert atmosphere of nitrogen, argon, or helium, or reducing atmosphere of hydrogen or inert gas containing hydrogen in consideration of the sinterability of the porous oxide particles, the material of the electrode substrate, and the like.

In the case where, for example, the porous oxide particles are liable to be reduced in the heat treatment of step (2), oxidizing atmosphere or inert atmosphere is selected.

On the other hand, in the case where the electrode substrate is liable to be oxidized and deteriorated, the heat treatment is preferably carried out in non-oxidizing inert gas atmosphere or in reducing atmosphere.

<Step (3)>

Step (3) is a step of heat-treating the electrode substrate, on which the porous oxide layer has been formed in step (2), in non-oxidizing atmosphere containing a carbon-containing compound so as to generate CNTs from the metal catalyst fine particles supported on the porous oxide particles.

The carbon-containing compound which is a carbon source of CNTs may be, for example, a hydrocarbon such as methane, ethane, propane, butane, benzene, toluene, xylene, hexane, or light oil; carbon monoxide; alcohol such as methanol, ethanol, propanol, or butanol; or the like. These carbon-containing compounds are used either alone or as a mixture to which a carrier such as argon is added.

Among the hydrocarbons, methane or ethylene is suitably used because carbon byproducts other than CNTs are less likely to be generated and the CNTs can be synthesized with a good yield.

When alcohol, preferably methanol or ethanol, especially preferably ethanol, is used as the carbon source, it is preferable because single-walled CNTs having a high quality can be grown at a low temperature as compared with the case where a hydrocarbon is used as the carbon-containing compound.

Here, the "non-oxidizing atmosphere" refers to atmosphere that does not contain oxidizing gas such as oxygen, so that inert atmosphere such as nitrogen, argon, or helium, or reducing atmosphere such as hydrogen or inert gas containing hydrogen is suitably selected.

In other words, the non-oxidizing atmosphere containing a carbon-containing compound is atmosphere in which the carbon-containing compound and inert gas such as argon or inert gas containing hydrogen coexist.

More specifically, it is possible to use a method of passing a hydrocarbon such as methane with inert gas such as argon or inert gas containing hydrogen used as carrier gas or, when the carbon-containing compound is alcohol, a method of passing a vapor of the alcohol while bubbling with the carrier gas or reducing the pressure of the inside of the reaction system to about 100 to 3000 Pa, or the like.

Synthesis of CNTs can be carried out, for example, by using a conventionally known method such as those disclosed in the following documents.

S. Maruyama, R. Kojima, Y. Miyauchi, S. Chiashi and M. Kohno, Chem. Phys. Lett. 360 (2002) 229.

S. Murakami, Y. Miyauchi, S. Chiashi, S. Maruyama, Chem. Phys. Lett. 374 (2003) 53.

In the following, the thermal CVD method (chemical vapor deposition method) that is suitable for synthesis of single-walled CNTs and that employs ethanol as the carbon-containing compound will be specifically described with reference to the drawings. Here, the method of step (3) is not limited to this method alone.

Figure 2:
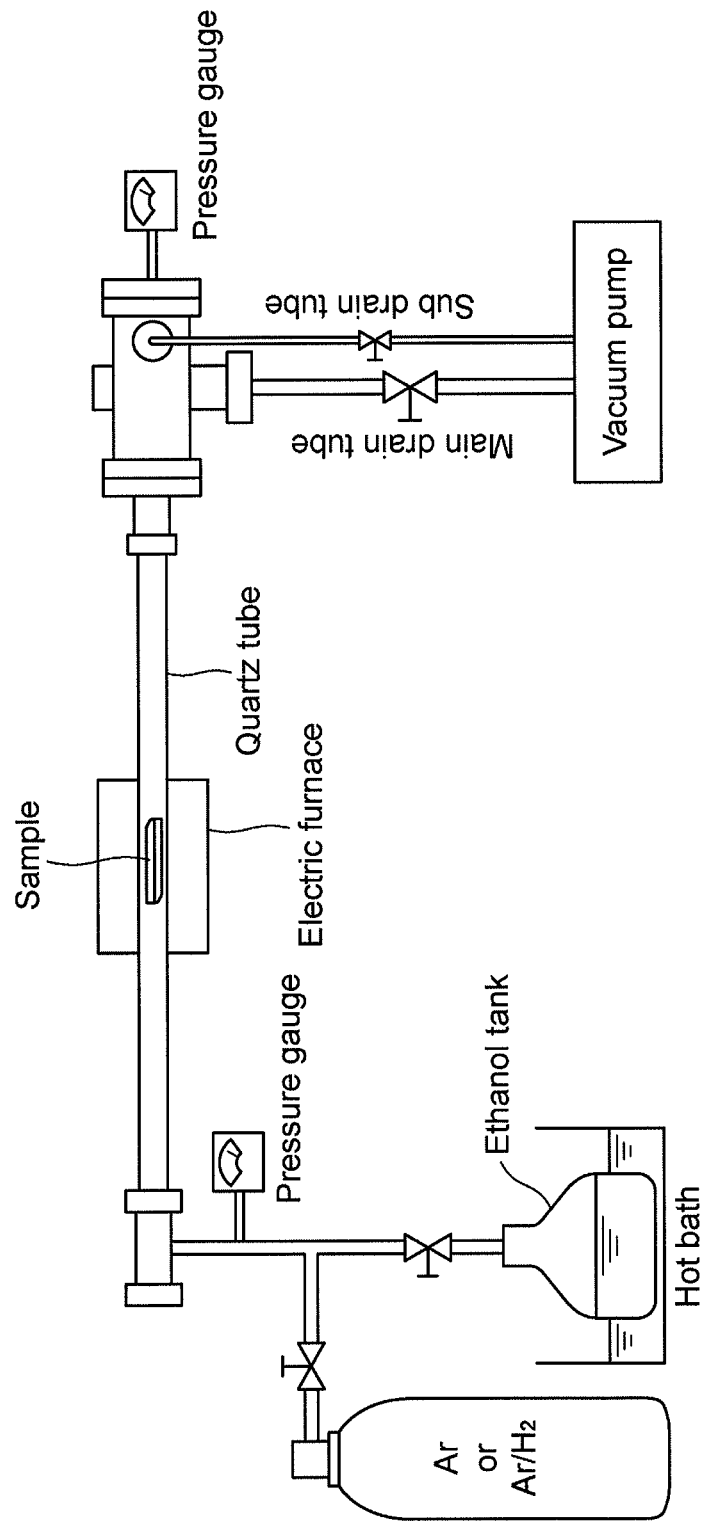
FIG. 2 is an outline configuration view of a CNT synthesis apparatus by the thermal CVD method (chemical vapor deposition method).

First, in a CNT synthesis apparatus shown in FIG. 2, an electrode substrate on which a porous oxide layer has been formed is placed in a reaction container made of quartz glass, and the temperature is raised to a predetermined temperature by an electric furnace while supplying argon gas with adjusted flow rate and pressure by gas supplying apparatus.

Subsequently, mixture gas of hydrogen/argon is supplied to the reaction container so as to activate the metal catalyst supported on the porous oxide material constituting the porous oxide layer. The hydrogen concentration is set so as to allow activation of the metal catalyst, and is generally 10 to 100 vol %.

Subsequently, an ethanol vapor or mixture gas of ethanol vapor/argon is supplied to the reaction container so as to bring the metal-based catalyst fine particles contained in the porous oxide layer of the electrode substrate into contact with the ethanol vapor to produce the CNTs.

Suitable conditions in the case of the thermal CVD method are a synthesis temperature of 600 to 900° C. (preferably 700 to 850° C.); a synthesis time of 5 to 60 minutes; and a synthesis pressure of 0.01 to 1 atm.

In addition, the ethanol supplying speed is suitably selected in consideration of the size of the reaction container, the gas concentration, and the like, and one example thereof is ethanol 200 sccm.

Among the aforementioned conditions, the synthesis temperature exerts an influence on the diameter of the generated CNTs, the generation of byproducts, and the like. When the synthesis temperature is less than 600° C., the growth speed of CNTs will be small, and the yield may decrease. When the synthesis temperature exceeds 900° C., the porous oxide material becomes liable to be thermally decomposed, and the metal catalyst particles get agglomerated to make the particle size thereof nonuniform. This may result in nonuniformity of the diameter and orientation property of the generated CNTs or decrease in the yield of the CNTs.

Here, the orientation property, the length, the density, and the growth position of the synthesized CNTs can be confirmed by the Raman spectroscopy, an atomic force microscope (AFM), a scanning electron microscope (SEM), or the like.

EXAMPLES

Hereafter, the present invention will be described further in detail by way of examples; however, the present invention is not limited to the following examples unless the gist thereof is changed.

The reagents and materials used in examples and comparative examples are as follows.

"reagents"

cobalt(II) acetate•tetrahydrate (99.0%, NACALAI TESQUE, INC.)

molybdenum(II) acetate (98.0%, NACALAI TESQUE, INC.)

ethanol (analytical grade, NACALAI TESQUE, INC.)

zeolite (Tosoh Corporation, HSZ-390HUA, pore diameter of 0.4 to 0.8 nm, specific surface area of 620 $m^2/g$ (by the BET method), crystal size of 0.3 μm)

activated alumina (Wako Pure Chemical Industries, Ltd., 90%, for column chromatography, about 30 mesh, particle size of 75 μm)

mesoporous silica (aluminosilicate) (Sigma Aldrich, specific surface area of 1000 $m^2/g$, pore diameter of 2 to 4 nm)

tetrachloroauric(III) acid trihydrate (chloroauric acid, 99.9%, Sigma Aldrich Co., Ltd.) palladium(II) chloride (Wako Pure Chemical Industries, Ltd., 99%)

hexachloroplatinic(IV) acid hexahydrate (platinic chloride, Wako Pure Chemical Industries, Ltd., 99.9%)

laccase (Lac, Daiwa Kasei Co., Ltd., derived from *Trametes* sp., EC 1.10.3.2)

fructose dehydrogenase (FDH, derived from *Gluconobacter* sp., Toyobo Co., Ltd., EC 1.1.99.11)

alcohol dehydrogenase (ADH, NACALAI TESQUE, INC., derived from yeasts, EC 1.1.1.1)

β-nicotinamide-adenine dinucleotide (NADH, NACALAI TESQUE, INC., purity of 90%) sodium lauryl sulfate (SDS, NACALAI TESQUE, INC., 99.5%)

"electrode substrate"
gold (99.9 to 99.999%, The Nilaco Corporation)
copper (99.9%, The Nilaco Corporation)
iron (99.5%, The Nilaco Corporation)
palladium (99.9%, The Nilaco Corporation)
nickel (99.9%, The Nilaco Corporation)

"evaluation apparatus"
  scanning electron microscope (SEM): Hitachi High-Technologies Corporation SU8000
  transmission electron microscope (TEM): JEOL Ltd. 2000FX
  Raman spectrometry apparatus: HORIBA, Ltd. LabRAM HR800 (laser wavelength: 514.5 nm or 532 nm)

"1. Fabrication of CNT Composite Electrode"
(Fabrication of CNT Composite Electrode 1)

First, cobalt(II) acetate·tetrahydrate and molybdenum acetate were dissolved in 10 mL of ethanol so as to attain 10 wt % and 1.4 wt %, respectively. Subsequently, 5 g of zeolite was added as porous oxide particles and was sufficiently mixed to let the solution permeate into the pores of the porous oxide particles. The obtained suspension was used as a catalyst coating liquid for generating CNTs in a slurry form.

Figure 3A:
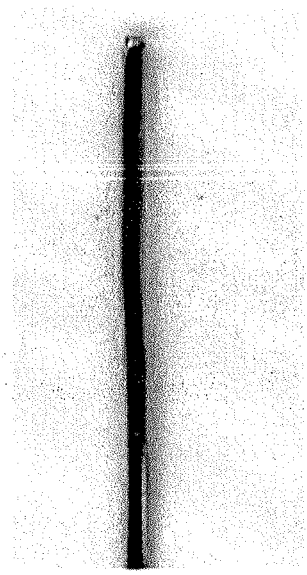
FIG. 3A is a photograph of an electrode (Au wire) before the surface layer containing CNTs is formed.

Subsequently, as an electrode substrate, an Au wire (purity: 99.999%) having a diameter of 0.8 mm and a length of 10 cm shown in FIG. 3A was prepared, and about 1 cm of the lower part of the Au wire was immersed in the catalyst coating liquid to perform dip-coating on the Au wire with the catalyst coating liquid.

The Au wire on which the catalyst coating liquid had been coated was put into a CVD apparatus having a construction shown in FIG. 2, and the temperature was raised to 850° C. at a temperature raising speed of about 40° C./min in Ar atmosphere. Here, in this temperature raising step, the volatile components such as ethanol are removed, and zeolite which is a porous oxide material closely adheres to the Au wire.

Subsequently, hydrogen was passed at 850° C. for 10 minutes to perform a reduction treatment, thereby to reduce the metal component contained in the catalyst coating liquid.

Figure 3B:
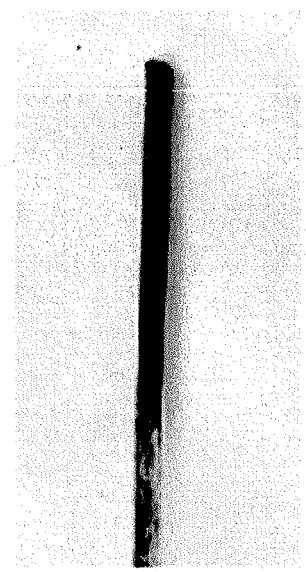
FIG. 3B is a photograph of an electrode (a CNT composite electrode 1, porous oxide material: zeolite) after the surface layer containing CNTs is formed.

Subsequently, after the reduction was carried out, mixture gas of hydrogen/ethanol at a volume ratio of 1/2 was passed at 850° C. for 10 minutes to obtain a CNT composite electrode 1. The external view of the CNT composite electrode 1 is shown in FIG. 3B.

Here, the metal component of the CNT composite electrode 1 (a different sample) after the reduction was evaluated by XRD, and it was confirmed that a CoMo alloy had been formed. In addition, by TEM observation, it was confirmed that the CoMo alloy was all made of fine particles of 5 nm or less.

(Fabrication of CNT Composite Electrode 2)

Figure 4:
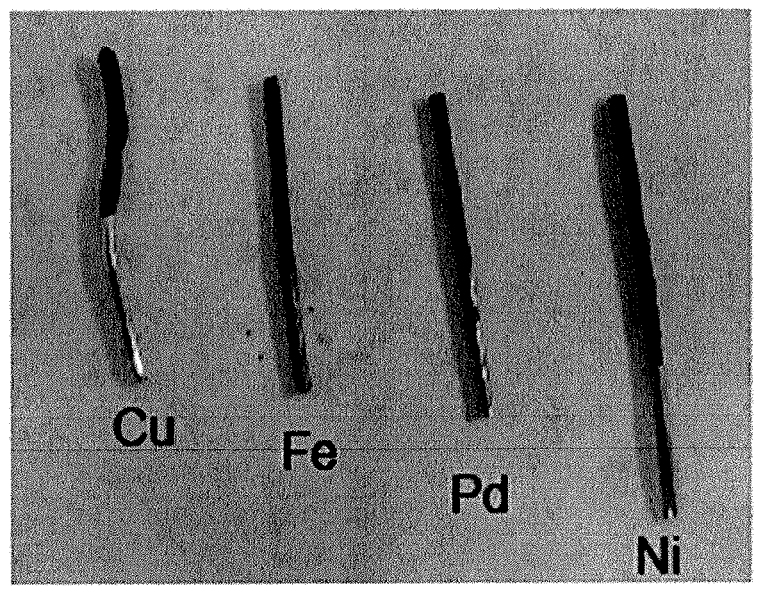
FIG. 4 is a photograph of CNT composite electrodes 2 to 5.

A CNT composite electrode 2 was obtained in the same manner as in the method of fabricating the CNT composite electrode 1 except that a Cu wire (diameter of 0.5 mm, length of about 4 cm) was used as the electrode substrate instead of the Au wire. The external view of the CNT composite electrode 2 is shown in FIG. 4.

(Fabrication of CNT Composite Electrode 3)

A CNT composite electrode 3 was obtained in the same manner as in the method of fabricating the CNT composite electrode 1 except that a Fe wire (diameter of 0.5 mm, length of about 4 cm) was used as the electrode substrate instead of the Au wire. The external view of the CNT composite electrode 3 is also shown in FIG. 4.

(Fabrication of CNT Composite Electrode 4)

A CNT composite electrode 4 was obtained in the same manner as in the method of fabricating the CNT composite electrode 1 except that a Pd wire (diameter of 0.5 mm, length of about 4 cm) was used as the electrode substrate instead of the Au wire. The external view of the CNT composite electrode 4 is also shown in FIG. 4.

(Fabrication of CNT Composite Electrode 5)

A CNT composite electrode 5 was obtained in the same manner as in the method of fabricating the CNT composite electrode 1 except that a Ni wire (diameter of 0.5 mm, length of about 5 cm) was used as the electrode substrate instead of the Au wire. The external view of the CNT composite electrode 5 is also shown in FIG. 4.

A surface layer derived from the formed CNTs and having a black color had been formed on the electrode substrate in any of the obtained CNT composite electrodes 1 to 5 as shown in FIGS. 3B and 4.

Figure 5A:
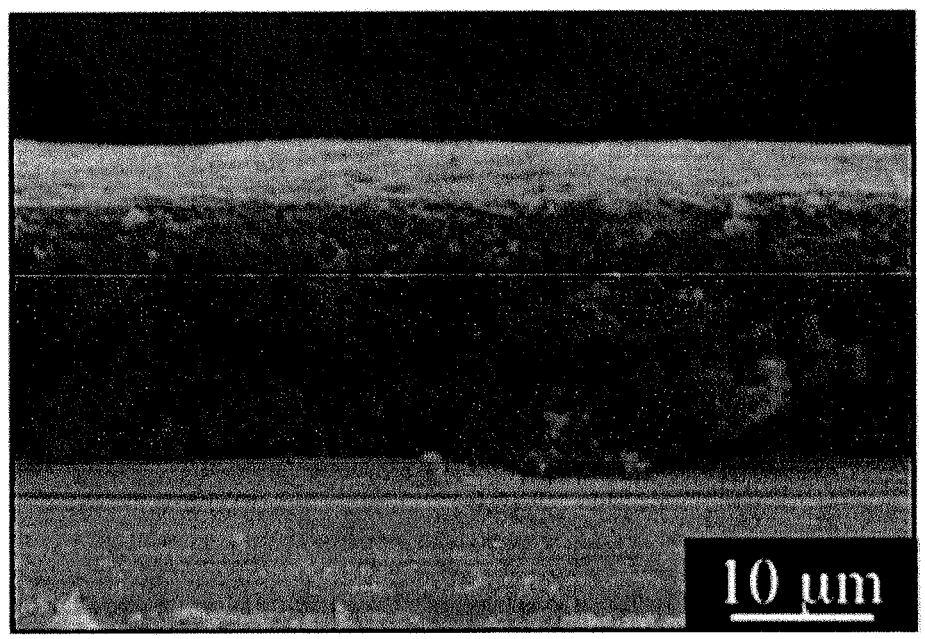
FIG. 5A shows a result of SEM (scanning electron microscope) observation of the surface layer in the CNT composite electrode 1 and is a SEM image of a boundary part between the electrode substrate (Au wire) and the surface layer.
Figure 5B:
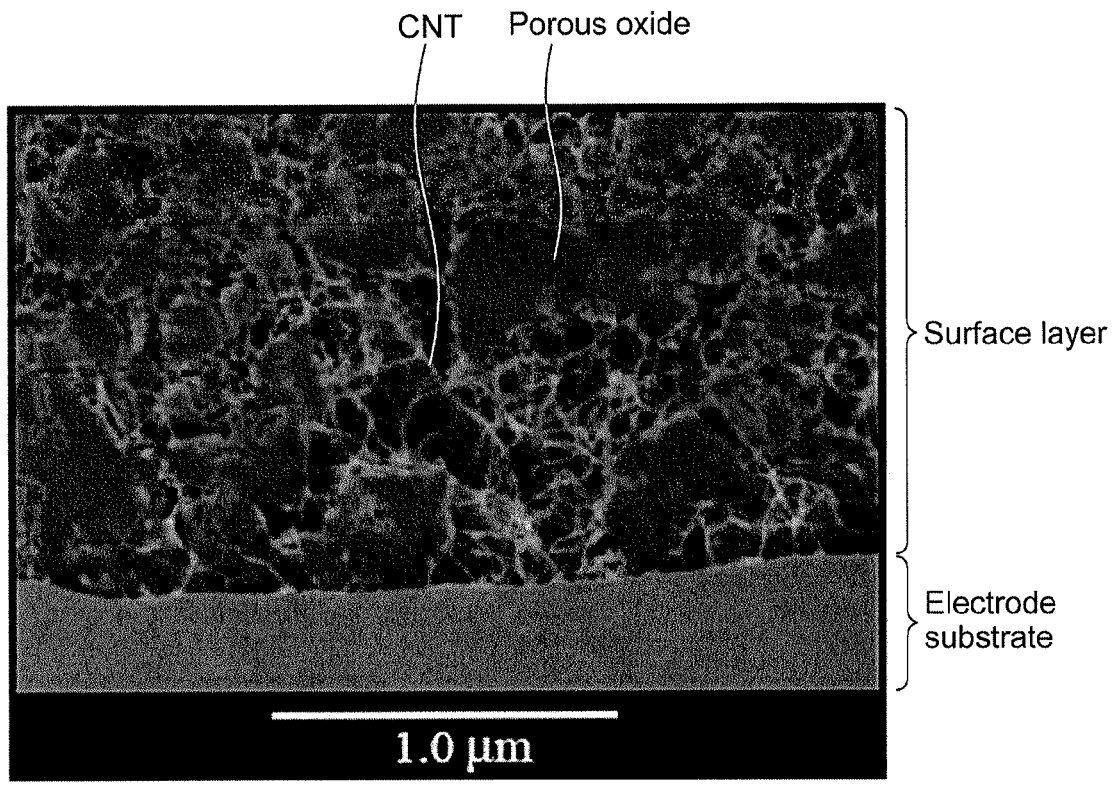
FIG. 5B is a SEM image (enlarged image) of a boundary part between the electrode substrate (Au wire) and the surface layer in the CNT composite electrode 1.
Figure 5C:
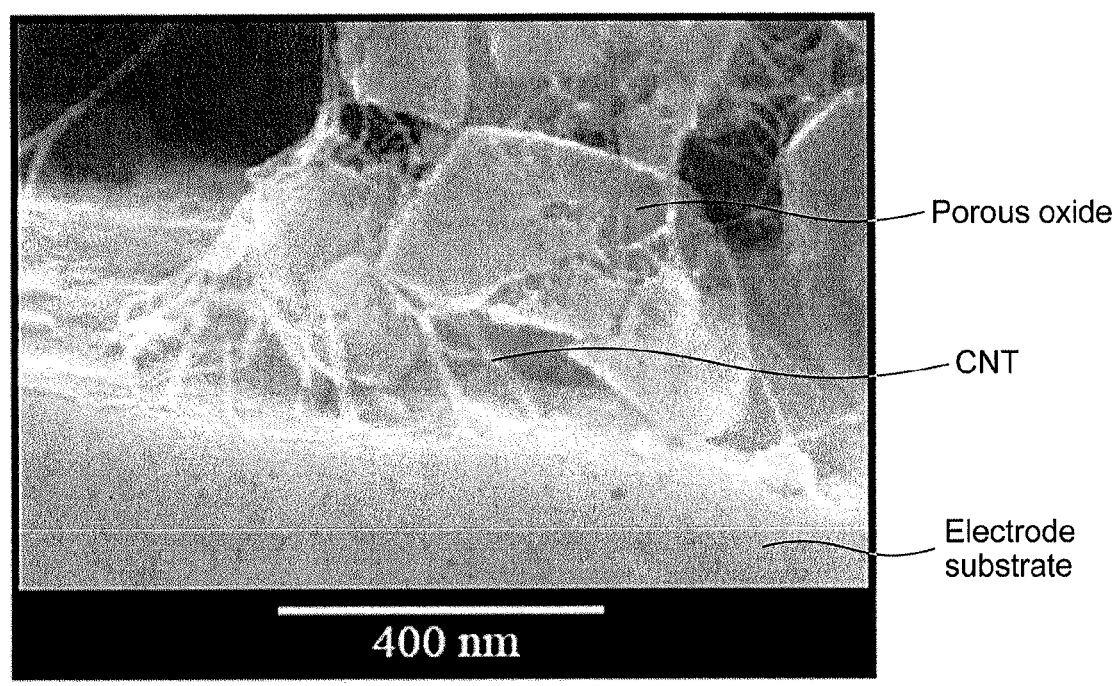
FIG. 5C is a SEM image (enlarged image) of a boundary part between the electrode substrate (Au wire) and the surface layer in the CNT composite electrode 1.
Figure 5D:
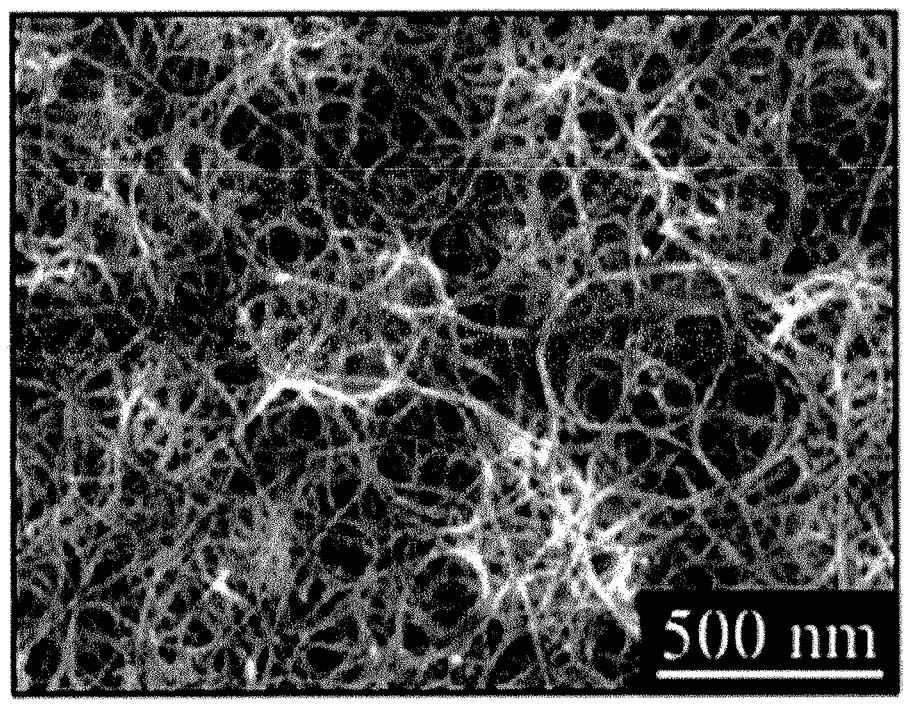
FIG. 5D is a SEM image (plan view) of the surface layer in the CNT composite electrode 1.

As a representative example, results of SEM observation of the surface layer formed on the CNT composite electrode 1 are shown in FIGS. 5A to 5D. Here, FIGS. 5A to 5C show a boundary part between the electrode substrate (Au wire) and the surface layer and the enlarged views thereof, and FIG. 5D shows a SEM image obtained by capturing an image of the surface layer from above.

Figure 6A:
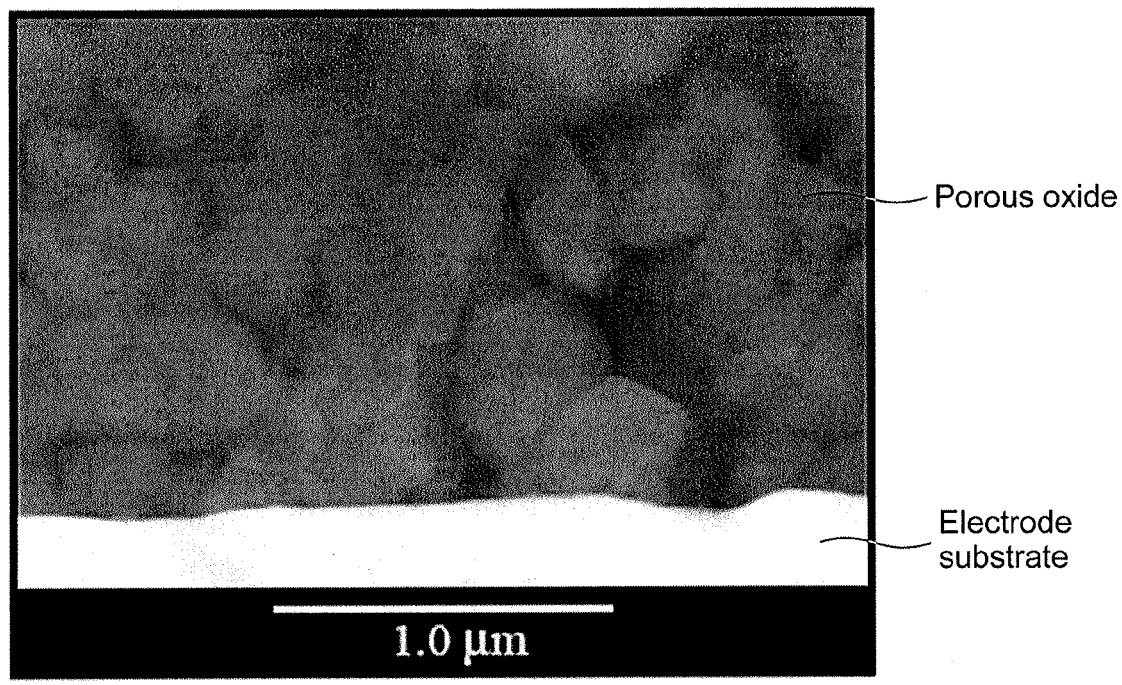
FIG. 6A is a SEM image of a boundary part between the electrode substrate (Au wire) and the porous oxide layer before the CNTs are grown.
Figure 6B:
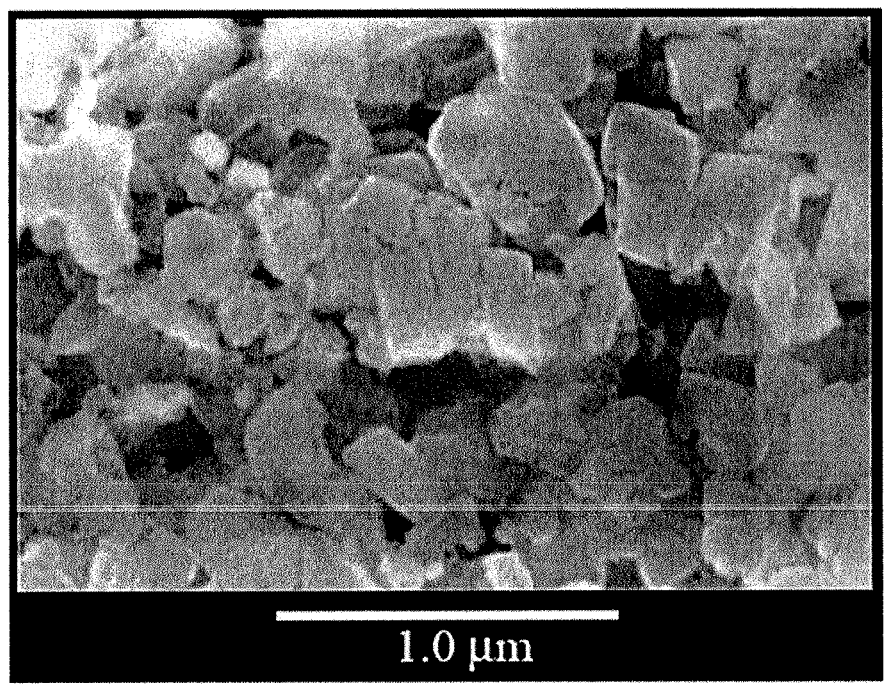
FIG. 6B is a SEM image (plan view) of the porous oxide layer of FIG. 6A.

For comparison, SEM images of the boundary part between the electrode substrate (Au wire) and the porous oxide layer before growing CNTs are shown in FIGS. 6A and 6B. Here, FIG. 6A shows a boundary part between the electrode substrate (Au wire) and the porous oxide layer and the enlarged view thereof, and FIG. 6B shows a SEM image obtained by capturing an image of the porous oxide layer from above.

As shown in FIG. 5A, the thickness of the surface layer formed on the Au wire was about 20 μm. From FIGS. 5B and 5C in which the cross-section of the surface layer is enlarged and FIG. 5D in which the surface is enlarged, it was confirmed that numerous CNTs having a jungle gym structure had been grown from the pores of the porous oxide material(zeolite).

Figure 7:
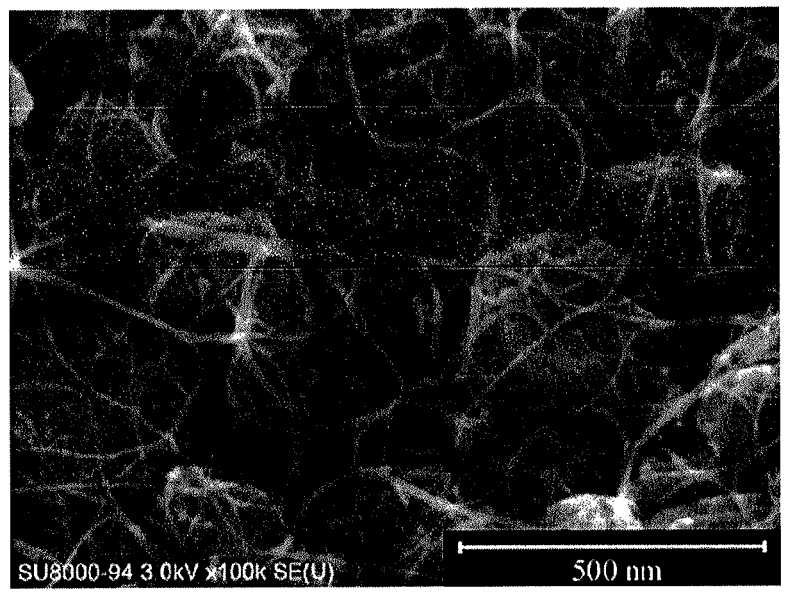
FIG. 7 is a SEM image (plan view) of the surface layer in the CNT composite electrode 1 in which the CNT production amount is suppressed.

The density of the generated CNTs was calculated using the TEM measurement results and, as a result, the density of the CNTs in the CNT composite electrode 1 was about $1 \times 10^{12}/cm^2$ In addition, as shown in FIG. 6A, in the porous oxide layer without having CNTs, the porous oxide particles constituting the porous oxide layer were connected with one another. In contrast, it has been found out that, in the CNT composite electrode 1, part of the porous oxide particles were separated by the growth of the CNTs (see FIG. 5B). In addition, FIG. 7 shows a SEM image of the surface layer of the CNT composite electrode manufactured by a method similar to that of the CNT composite electrode 1 except that mixture gas in which the volume ratio of hydrogen/ethanol was 1/5 was used. It will be understood that, as compared with the CNT composite electrode 1, the amount of generated CNTs is clearly smaller. Here, the density of the CNTs calculated by a method similar to the above was about $2 \times 10^{10}/cm^2$.

In addition, as shown in FIG. 7, separation of the porous oxide particles constituting the surface layer was confirmed though the density of generated CNTs was small.

In addition, as shown in FIG. 5C, it was confirmed that part of the CNTs formed in the surface layer and the electrode substrate were in contact with each other. Further, it was confirmed by eye inspection that the CNTs remained in the electrode substrate after the surface layer in which the CNTs had been formed was stripped off. From this, it was confirmed that part of the grown CNTs were embedded in the electrode substrate.

Figure 5E:
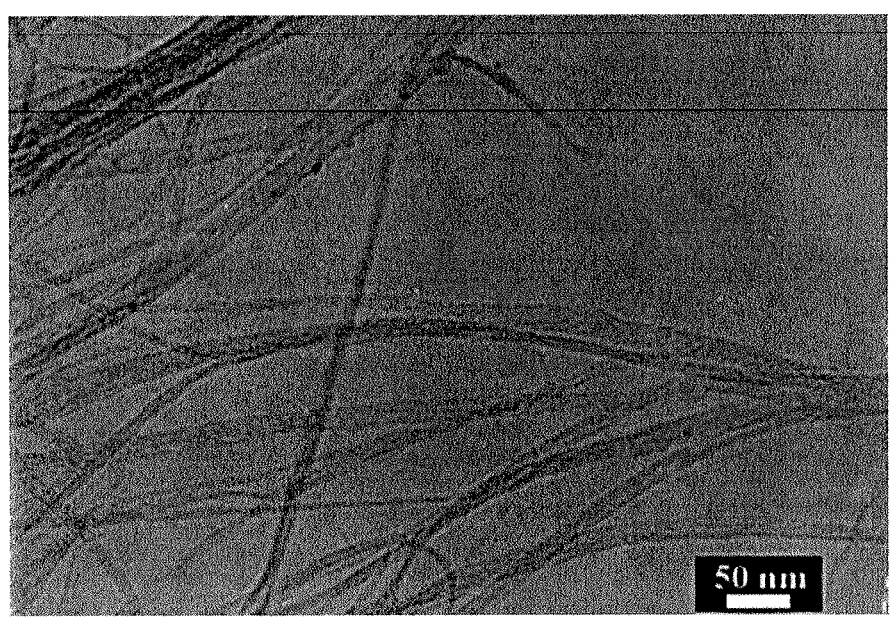
FIG. 5E is a TEM (transmission electron microscope) image of the carbon nanotubes of the surface layer in the CNT composite electrode 1.

FIG. 5E shows a result of TEM observation of the generated CNTs in the CNT composite electrode 1. The diameter of the generated CNTs was about 1 nm, and those CNTs were in a bundle form of 20 nm or less. Here, at least 70% or more of the total number of the observed CNTs had a diameter of about 1 nm.

Figure 8:
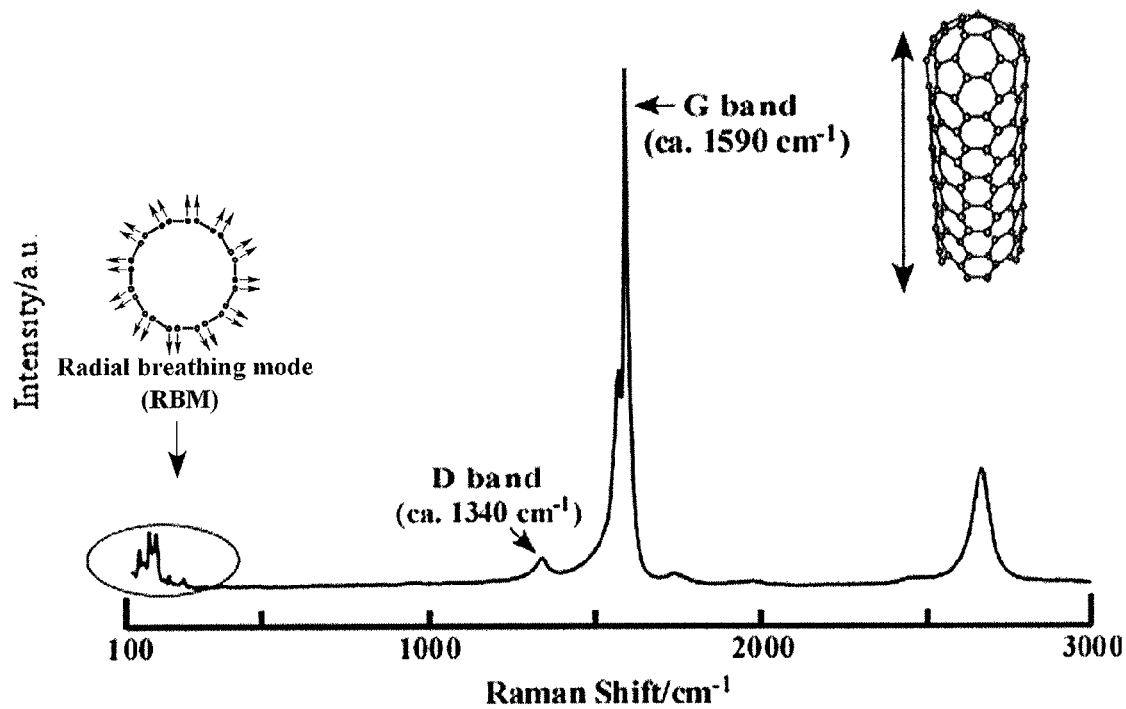
FIG. 8 shows a result of evaluating the surface layer in the CNT composite electrode 1 by the Raman spectroscopy (laser wavelength: 514.5 nm).

FIG. 8 shows a result of Raman spectrometry on the surface layer. Here, for Raman spectrometry, a laser wavelength of 514.5 nm was used.

As shown in FIG. 8, a peak derived from the graphene structure, which is referred to as a G-band, was observed in the vicinity of 1590 $cm^{-1}$. In addition, a broad peak derived from amorphous carbon or CNTs having a defective structure, which is referred to as a D-band, was observed in the vicinity of 1340 $cm^1$. Here, the crystal quality of CNTs is evaluated by the intensity ratio of the G-band to the D-band. It is considered that, according as the G/D ratio is larger, the CNTs are less defective and have higher quality.

Since the G/D ratio of the CNTs of the CNT composite electrode 1 was about 20 to 30, the CNTs were confirmed to be non-oxidized type CNTs having less amount of defects. In addition, it appears that most of the formed CNTs are single-walled CNTs judging from the fact that the half-value width of the peak referred to as a 2D(G')-band in the vicinity of 2700 $cm^{-1}$ is as sharp as about 50 $cm^{-1}$, and further that an RBM (Radial breathing mode) of the peak dependent on the diameter of the CNTs observed at 100 to 200 $cm^{-1}$ is definitely observed, and from the diameter (about 1 nm) of the CNTs observed in the TEM described above.

(Fabrication of CNT Composite Electrode 6)

First, cobalt(II) acetate•tetrahydrate and molybdenum(II) acetate were dissolved in 10 mL of ethanol so as to attain 10 wt % and 1.4 wt %, respectively. Subsequently, 5 g of activated alumina was added as porous oxide particles and mixed to obtain a catalyst coating liquid for generating CNTs in a slurry form.

With this catalyst coating liquid, an Au wire (99.999%, diameter of 0.8 mm, length of 10 cm) was subjected to dip-coating under the conditions similar to those of the method for fabricating the CNT composite electrode 1, and further, synthesis of CNTs was carried out to fabricate a CNT composite electrode 6.

On the formed surface layer, TEM observation and Raman spectrometry (laser wavelength of 532 nm) were carried out.

Figure 9A:
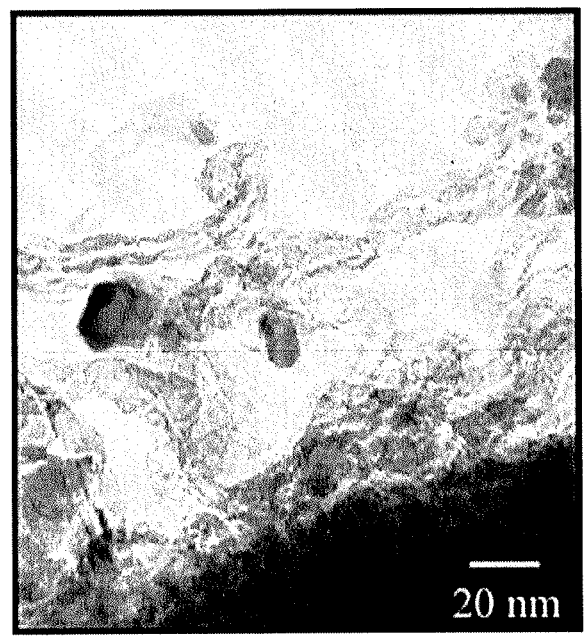
FIG. 9A is a TEM image of carbon nanotubes of a surface layer in a CNT composite electrode 6 (porous oxide material: activated alumina).

FIG. 9A shows a result of TEM observation of the surface layer formed on the CNT composite electrode 6. As will be understood from FIG. 9A, multi-walled CNTs were observed in the CNT composite electrode 6.

Figure 9B:
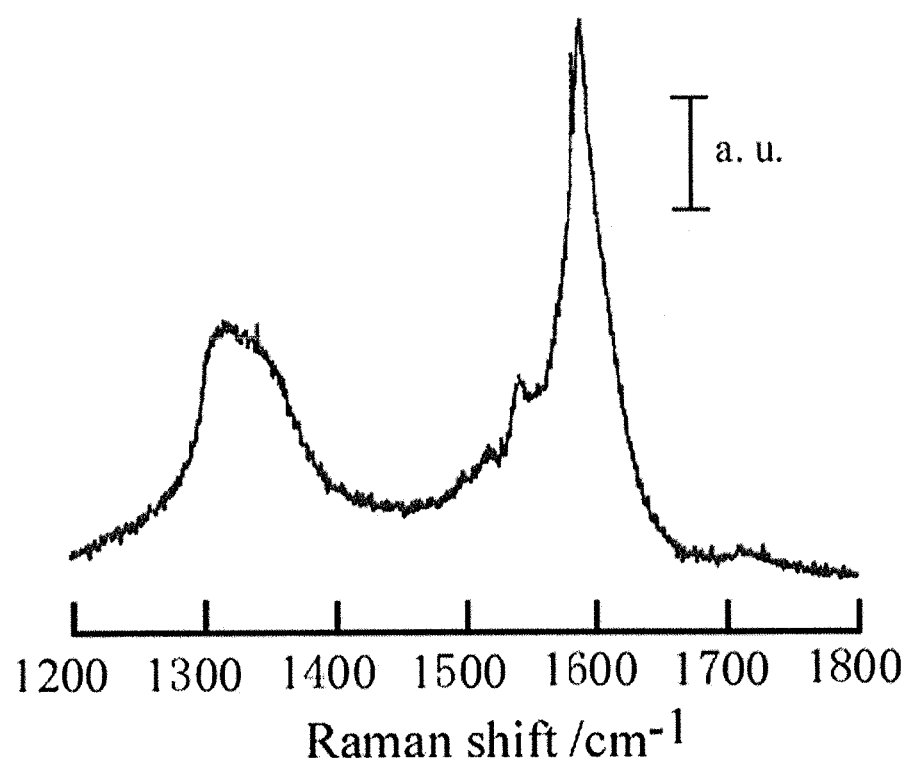
FIG. 9B shows a result of evaluating the surface layer in the CNT composite electrode 6 by the Raman spectroscopy (laser wavelength: 532 nm).

In addition, as shown in FIG. 9B, by Raman spectrometry on the surface layer, a G-band derived from the CNTs was observed.

(Fabrication of CNT Composite Electrode 7)

First, cobalt(II) acetate•tetrahydrate and molybdenum(II) acetate were dissolved in 10 mL of ethanol so as to attain 10 wt % and 1.4 wt %, respectively. Subsequently, 5 g of mesoporous silica was added as porous oxide particles and mixed to obtain a catalyst coating liquid for generating CNTs in a slurry form.

With this catalyst coating liquid, an Au wire (99.999%, diameter of 0.8 mm, length of 10 cm) was subjected to dip-coating under the conditions similar to those of the method for fabricating the CNT composite electrode 1, and further, synthesis of CNTs was carried out to fabricate a CNT composite electrode 7.

Figure 10:
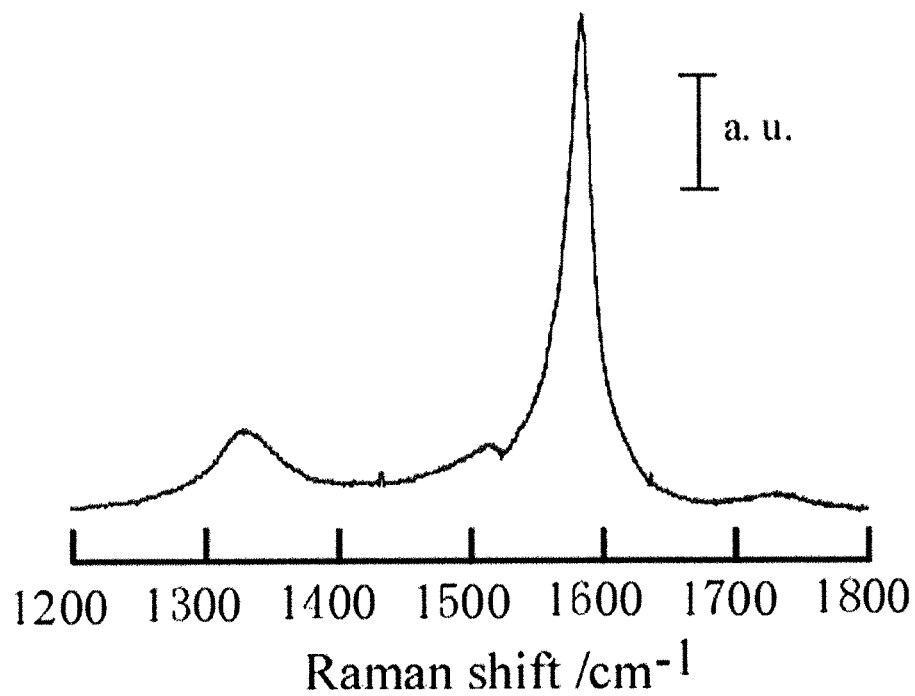
FIG. 10 shows a result of evaluating a surface layer in a CNT composite electrode 7 by the Raman spectroscopy (laser wavelength: 532 nm).

On the formed surface layer, Raman spectrometry (laser wavelength of 532 nm) was carried out. As a result, a G-band derived from the CNTs was observed as shown in FIG. 10.

"2. Electrochemical Evaluation"

(Evaluation 1-1)

Electrochemical oxidation behavior of NADH was evaluated by using the CNT composite electrode 1 described above and other electrodes for comparison as electrodes for evaluation.

The electrodes for evaluation that were put to use are shown below.

(a) (non-oxidized type) CNT composite electrode 1 (apparent electrode area: 0.25 $cm^2$)
(b) highly oriented pyrolytic graphite (HOPG, Panasonic Corporation, electrode area: 0.28 $cm^2$)
(c) glassy carbon (GC, TOKAI CARBON CO., LTD., electrode area: 0.07 $cm^2$)
(d) plastic formed carbon (PFC, Mitsubishi Pencil Co., Ltd., electrode area: 0.28 $cm^2$)
(e) Au wire (99.999%, The Nilaco Corporation, electrode area: 0.02 $cm^2$)

Here, as the CNT composite electrode 1, one in which contamination of the surface of the formed CNTs was avoided was used.

The measurement conditions are as follows.
(cell construction) three-electrode type cell
working electrode: CNT composite electrode 1
counter electrode: platinum plate
reference electrode: silver/silver chloride (saturated KCl) electrode
solution: 10 mM NADH/phosphate buffer solution (pH 7)
electric potential sweep rate: 20 mV/sec The results are shown in FIG. 11.

Figure 11:
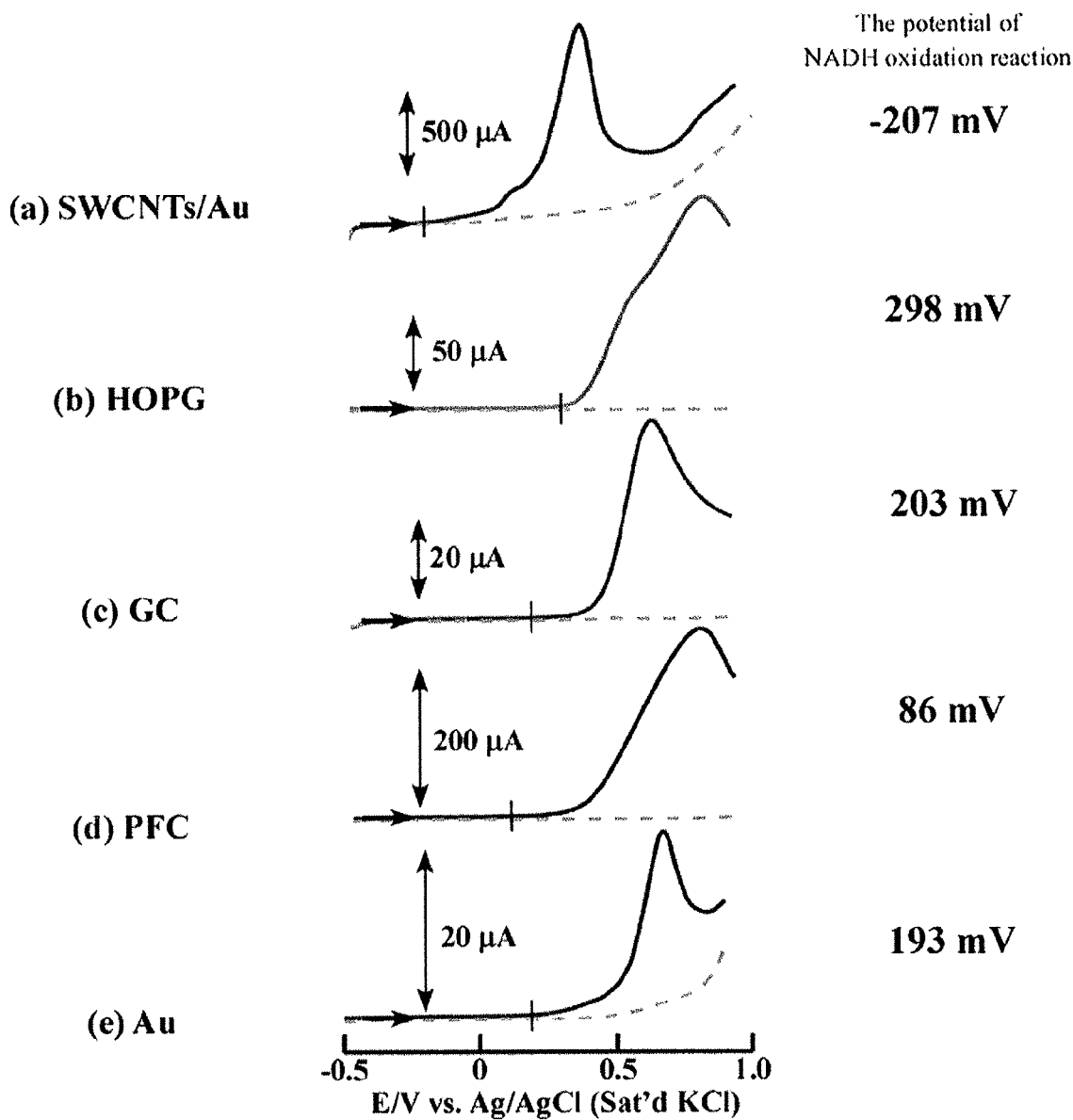
FIG. 11 shows a result of comparing the behavior of oxidation reaction of a reduced form (NADH) of β-nicotinamide-adenine dinucleotide on the CNT composite electrode 1 (SWCNTs/Au) with that of other carbon electrodes and gold electrodes.

From the background electric current and electric potential curve in the solution that does not contain NADH of FIG. 11, a good electrical connection between the substrate metal and the CNTs will be found out. In the case where a large resistance component is contained, for example, in the case where the electrical connection between the substrate metal and the CNTs is not good, linear increase in the electric current when going from left to right in the positive electric potential and linear decrease in the electric current when going from right to left in the negative electric potential are supposed to be observed; however, such decrease was not observed at all, so that it will be understood that a good electrical connection between the substrate metal and the CNTs was established.

With respect to the CNT composite electrode 1, an oxidation electric current accompanying the oxidation reaction of NADH on the electrode was observed from −207 mV.

On the other hand, with respect to the HOPG, GC, PFC, and Au (electrode substrate of CNT composite electrode 1) which were other carbon electrodes, an oxidation electric current accompanying the oxidation reaction of NADH was observed from 298, 203, 86, and 193 mV, respectively.

Thus, it has been confirmed that, in the case of the CNT composite electrode 1, an oxidation reaction of NADH starts at a more negative electric potential than in the case of other electrodes for comparison.

(Evaluation 1-2)

Generation of $NAD^+$ is expected as a product of the oxidation reaction of NADH on the electrode. Whether $NAD^+$ was actually generated or not in the oxidation reaction of NADH by the CNT composite electrode 1 described above was studied by using alcohol dehydrogenase (ADH).

Figure 12A:
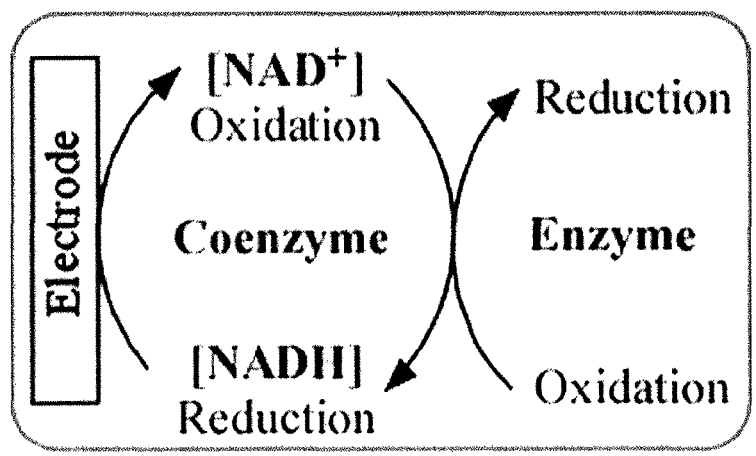
FIG. 12A is a scheme representing a redox cycle by NADH and alcohol dehydrogenase (ADH) on the electrode surface.

When $NAD^+$ is generated as an oxidation product of NADH in the oxidation reaction on the electrode, an increase in the oxidation electric current of NADH observed at the electrode is anticipated because ethanol which is a substrate of ADH is oxidized by ADH and the ADH in a reduced form is re-oxidized by $NAD^+$ as in the scheme shown in FIG. 12A.

Figure 12B:
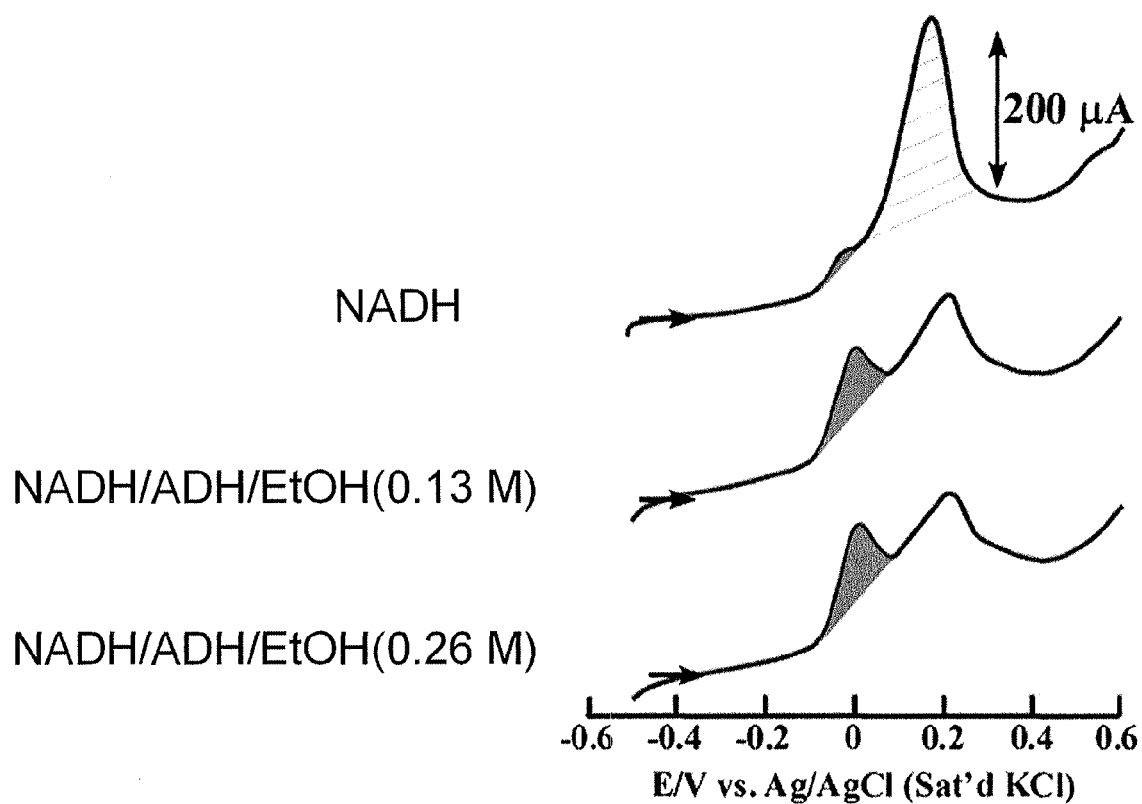
FIG. 12B shows a result of evaluating the oxidation reaction of NADH in the coexistence of ADH and ethanol which is a substrate of ADH using the CNT composite electrode 1 (SWCNTs/Au).

The evaluation results are shown in FIG. 12B.

With respect to the CNT composite electrode 1, in accordance with an increase in the ethanol concentration of the substrate, an increase in the oxidation electric current in the vicinity of 0 V was observed. On the other hand, no increase in the oxidation electric current in the vicinity of 0.2 V was observed, so that it has been shown that the oxidation reaction of NADH occurring at this electric potential does not accompany the generation of $NAD^+$. The oxidation reaction of NADH in vivo is known to occur in the vicinity of −0.5 V. In addition, it is known that, in the oxidation reaction of NADH under large overvoltage conditions, dimers of $NAD^+$ are liable to be generated. Therefore, by the oxidation electric current of NADH in the vicinity of 0.2 V, generation of dimers is anticipated.

On the other hand, in the cases where the HOPG, GC, PFC, and Au electrodes were used, no increase in the oxidation electric current of NADH shown in FIG. 11 in the coexistence of NADH, ethanol, and ADH was observed at all, so that it has been shown that NAD was not generated.
(Evaluation 2)

Figure 13:
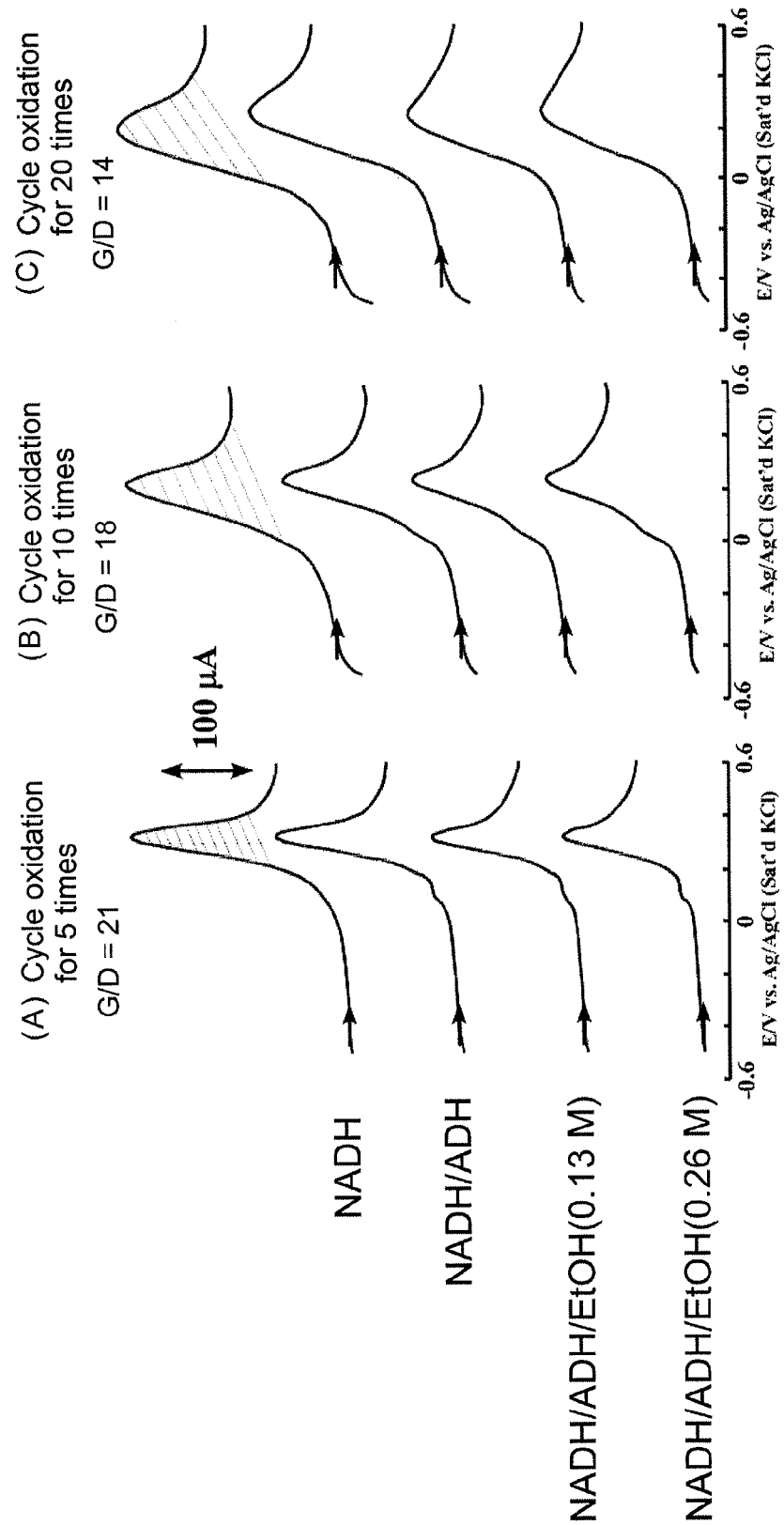
FIG. 13 shows a result of evaluating the oxidation reaction of NADH on (oxidized type) CNT composite electrodes A to C.

The aforementioned (non-oxidized type) CNT composite electrode 1 was electrochemically oxidized under the following conditions to fabricate the oxidized type CNT composite electrodes A to C shown in Table 1.
(Electrochemical Oxidation Conditions)
electrolytic solution (phosphate buffer solution (pH 7, 0.1 M))
electric potential sweep rate: 20 mV/sec
electric potential sweeping range: 0 V to +1.3 V (vs. Ag/AgCl (saturated KCl))
number of cycle oxidation:
CNT composite electrode A: 5 times
CNT composite electrode B: 10 times
CNT composite electrode C: 20 times FIG. 13 shows a result of performing an evaluation similar to that of (Evaluation 1-2) described above by using the obtained (oxidized type) CNT composite electrodes A to C. In addition, a result of evaluation by Raman spectroscopy of G/D ratio of the CNT composite electrodes A to C is shown in Table 1 together with the CNT composite electrode 1:

With respect to the CNT composite electrode A, a little oxidation electric current was observed in the vicinity of 0.1 V in the presence of ethanol as a substrate. On the other hand, no increase in the oxidation electric current in the vicinity of 0.2 V was observed at all, thereby showing that the NADH oxidation reaction occurring at this electric potential does not accompany the generation of $NAD^+$. Similarly, the CNT composite electrodes B and C were studied, and no increase in the oxidation electric current was observed at all, so that it has been shown that the product by the NADH oxidation reaction on these electrodes is not $NAD^+$. The above shows that the non-oxidized type CNT electrode is useful for the $NAD^+$ generation by the NADH oxidation reaction.

TABLE 1

| | Oxidized type/ non-oxidized type | Number of cycle oxidation | G/D |
|---|---|---|---|
| CNT composite electrode 1 | Non-oxidized type | 0 | 26 |
| CNT composite electrode A | Oxidized type | 5 | 21 |
| CNT composite electrode B | Oxidized type | 10 | 18 |
| CNT composite electrode C | Oxidized type | 20 | 14 |

"3. Fabrication of CNT Composite Electrode Carrying Metal Fine Particles"
(Fabrication of Au-CNT Composite Electrode (I))

An Au-CNT composite electrode 1 was fabricated by the following procedure.

The CNT composite electrode 1 (non-oxidized type) having a clean surface immediately after synthesis was immersed in 0.5 M sulfuric acid containing 5 mM of chloroauric acid for 30 minutes to fabricate an Au-CNT composite electrode (I). Here, the electrode fabrication was carried out at an ordinary temperature under an ordinary pressure under shielding from light.

Figure 14:
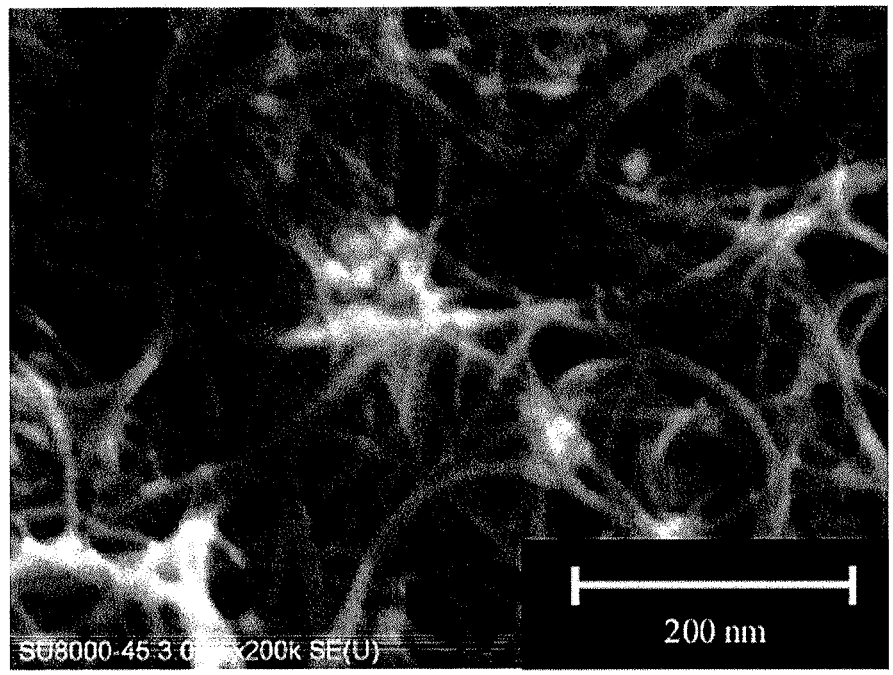
FIG. 14 is a SEM image of an Au-CNT composite electrode (I).
Figure 15:
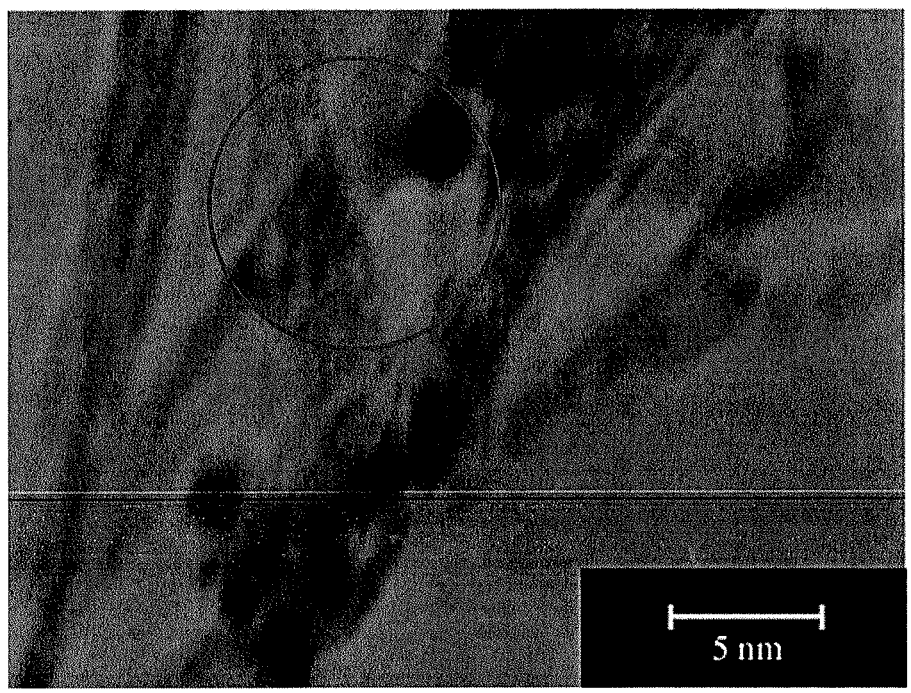
FIG. 15 is a TEM image of the Au-CNT composite electrode (I).

The result of SEM observation of the Au-CNT composite electrode (I) is shown in FIG. 14, and the result of TEM observation is shown in FIG. 15.

In the SEM image, adsorption of fine adhered substances was observed on the CNT surface. By the TEM image of the CNT surface, a state in which gold fine particles having a diameter of 10 nm or less (mainly distributed at 2 nm or less) had been fabricated at a high density and highly dispersed was observed.
(Fabrication of Au-CNT Composite Electrode (II))

Immersion into an aqueous solution of SDS for 30 minutes and rinsing with pure water were carried out before immersion into chloroauric acid. Thereafter, steps similar to those of the method for manufacturing the Au-CNT composite electrode (I) were carried out to obtain an Au-CNT composite electrode (II).

Figure 16:
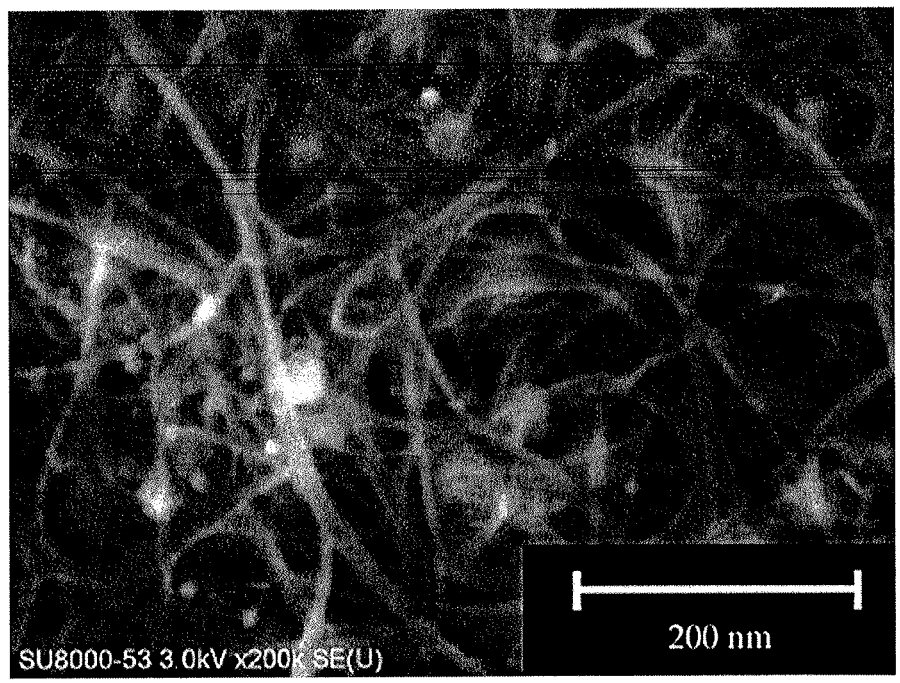
FIG. 16 is a SEM image of an Au-CNT composite electrode (II).

FIG. 16 shows a result of SEM observation. From the SEM image, gold fine particles having a diameter of about 10 nm or more were observed.
(Fabrication of Au-CNT Composite Electrode (III))

The CNT composite electrode 1 in which the CNT surface had been contaminated with organic substances and others in ambient air by storage in ambient air (for one day) was used. An Au-CNT composite electrode (III) was obtained by carrying out steps similar to those of the method for manufacturing the Au-CNT composite electrode (I).

Figure 17:
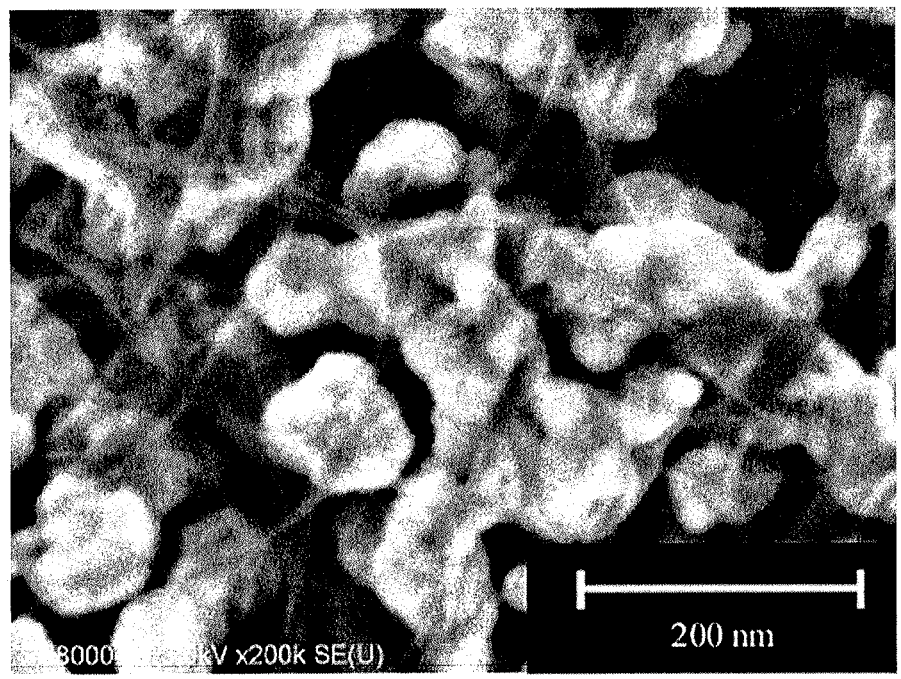
FIG. 17 is a SEM image of an Au-CNT composite electrode (III).

FIG. 17 shows a result of SEM observation. From the SEM image, gold fine particles having a diameter of 50 to 200 nm were observed.
(Fabrication of Pd-CNT Composite Electrode (I))

Instead of chloroauric acid, palladium chloride was used. A Pd-CNT composite electrode (I) was obtained by carrying out steps similar to those of the method for manufacturing the Au-CNT composite electrode (I).

Figure 18:
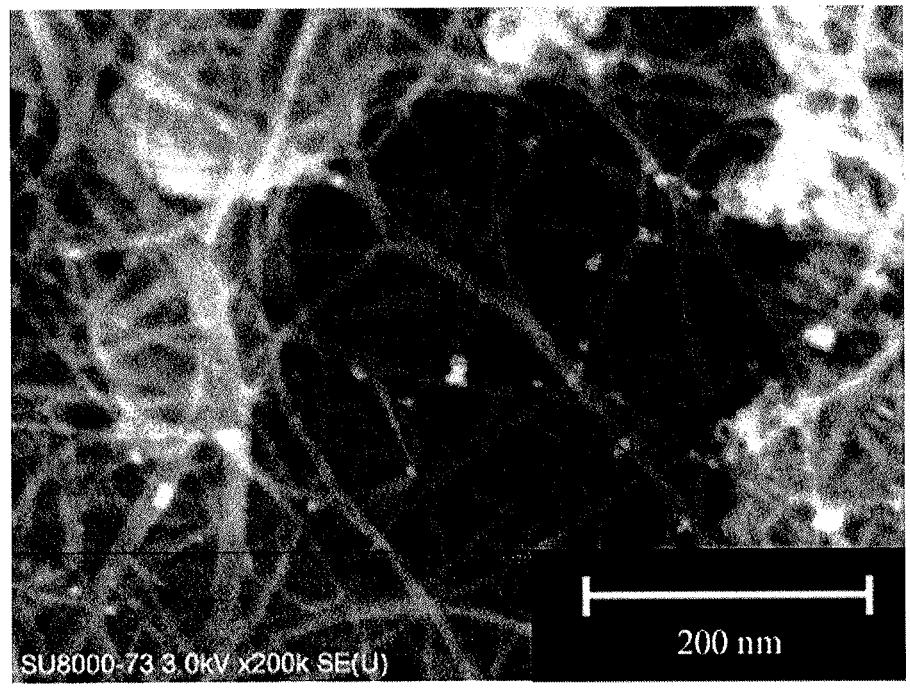
FIG. 18 is a SEM image of a Pd-CNT composite electrode (I).

FIG. 18 shows a result of SEM observation. From the SEM image, palladium fine particles having a diameter of about 10 nm or less were observed. In addition, though not definite, a state in which numerous fine particles were adsorbed onto the CNT surface was understood from the SEM image.
(Fabrication of Pd-CNT Composite Electrode (II))

Instead of chloroauric acid, palladium chloride was used. A Pd-CNT composite electrode (II) was obtained by carrying out steps similar to those of the method for manufacturing the Au-CNT composite electrode (III).

Figure 19:
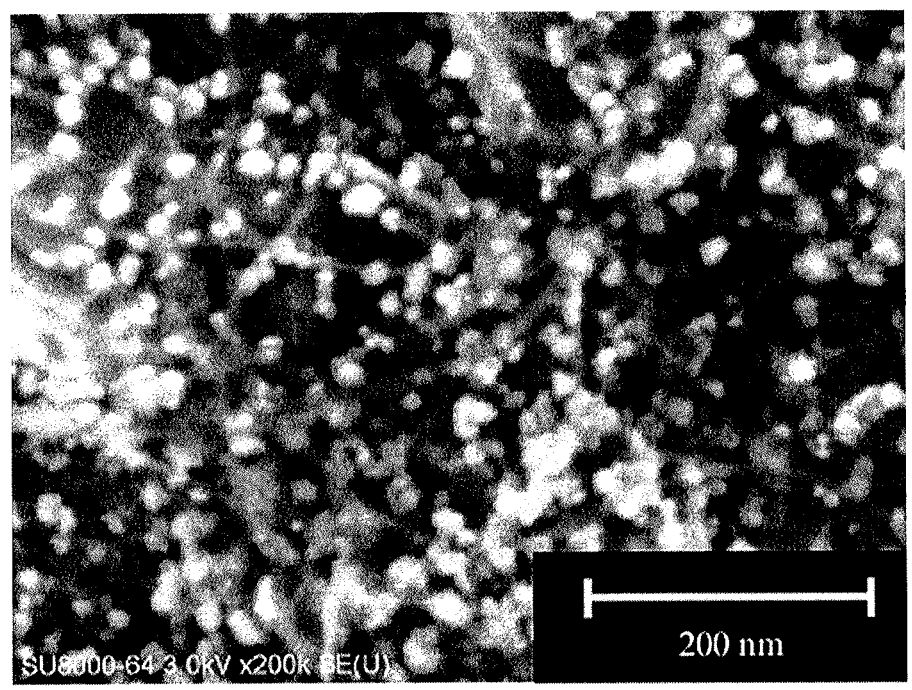
FIG. 19 is a SEM image of a Pd-CNT composite electrode (II).

FIG. 19 shows a result of SEM observation. From the SEM image, a state in which palladium fine particles having a diameter of about 10 to 20 nm had been fabricated at a high density and highly dispersed was observed.

"4. Application Examples"

(4-1. Evaluation as Electrode for Sugar-Oxygen Fuel Cell)

By using the aforementioned CNT composite electrode, a sugar-oxygen fuel cell can be fabricated.

Figure 20A:
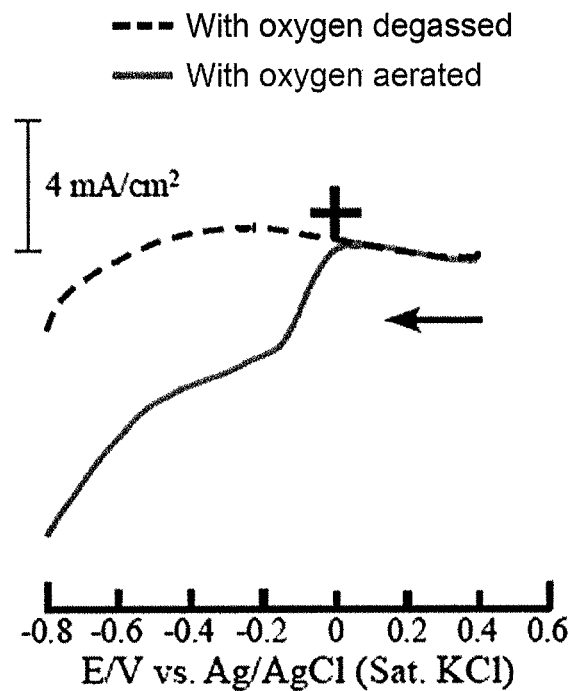
FIG. 20A is a graph showing an electrochemical catalytic oxygen reduction reaction of the CNT composite electrode 1.
Figure 20B:
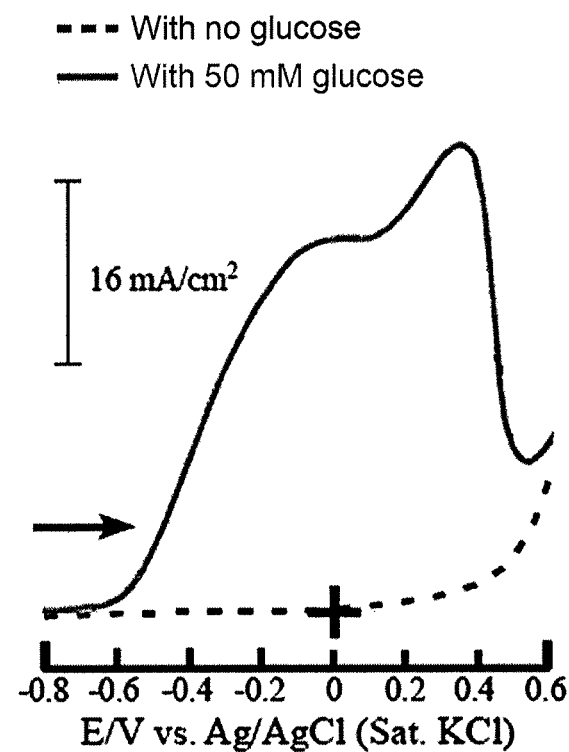
FIG. 20B is a graph showing a catalytic oxidation reaction of glucose on the Au-CNT composite electrode (I).

FIG. 20A shows a result of performing evaluation of an oxygen reduction reaction using the CNT composite electrode 1, and FIG. 20B shows a result of studying a glucose oxidation reaction using the Au-CNT composite electrode 1. The measurement conditions are shown in the figures.

From FIGS. 20A and 20B, it will be understood that the oxygen reduction electric potential serving as a cathode electrode is at a more noble electric potential than the glucose oxidation electric potential serving as an anode electrode. For this reason, a sugar-oxygen fuel cell having an electromotive force of about 0.8 V can be fabricated by using the CNT composite electrode 1 and the Au-CNT composite electrode 1.

(4-2. Application as Dye-Sensitized Solar Cell)

Hereafter, an example is shown in which the CNT composite electrode of the present invention is applied to an electrode (a cathode) for a dye-sensitized solar cell.

As a cathode, a CNT composite electrode carrying Pt fine particles on the CNTs was used.

Figure 21A:
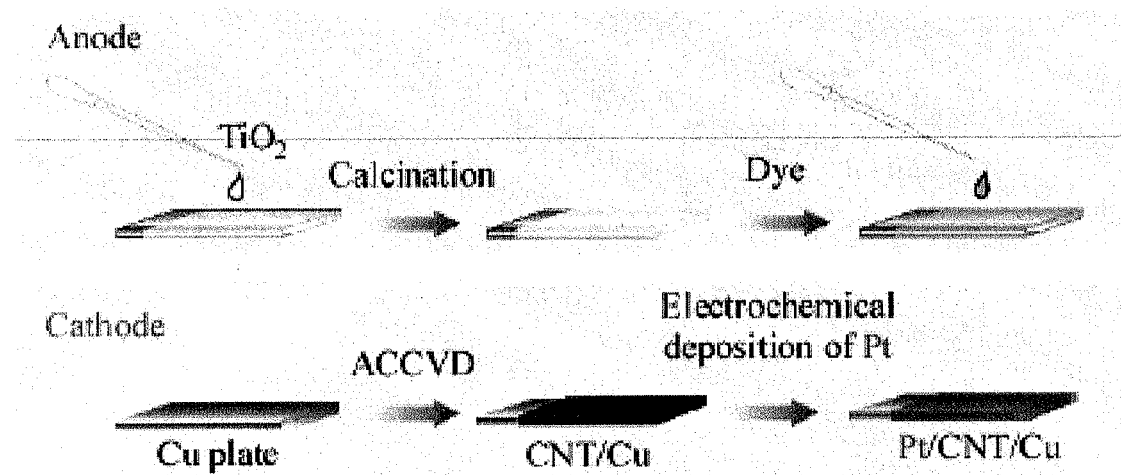
FIG. 21A is a schematic view of a method for fabricating an electrode of a dye-sensitized solar cell using a CNT composite electrode of the present invention.
Figure 21B:
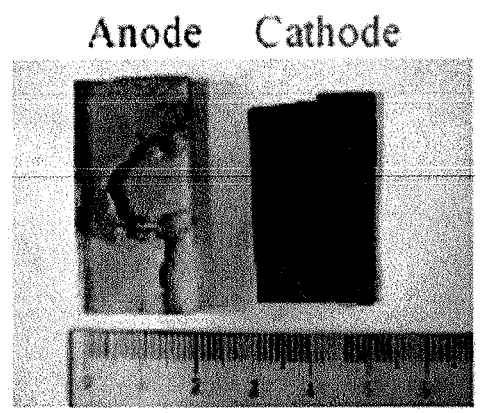
FIG. 21B is a photograph of an anode and a cathode in the dye-sensitized solar cell using the CNT composite electrode of the present invention.

First, as an electrode substrate, dip-coating and further synthesis of CNTs were carried out on a copper plate (20×40 mm) under conditions similar to those of the aforementioned method for fabricating the CNT composite electrode 1, so as to fabricate a CNT composite electrode having a surface layer containing single-walled CNTs on the copper plate. Further, for improvement in the electric conductivity, platinum fine particles were fabricated on the CNTs by the electrochemical reduction method. Specifically, platinum fine particles were fabricated on the CNTs by applying an electric potential of 0 V (vs. Ag/AgCl (saturated KCl)) to the CNT composite electrode in a 0.1 M sulfuric acid solution of 1 mM hexachloroplatinic (IV) acid. The obtained electrode was used as a cathode. FIG. 21A shows a schematic view of cathode fabrication, and FIG. 21B shows a photograph of the cathode after fabrication.

Figure 21C:
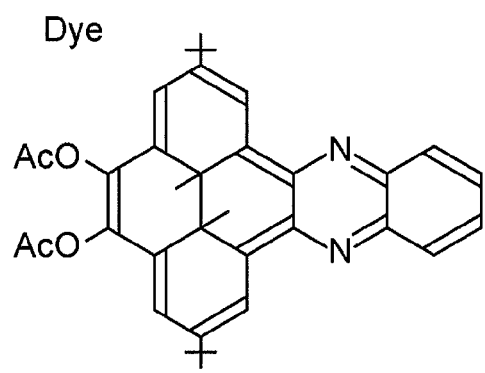
FIG. 21C shows a chemical structure of a dye applied to the anode.

As an anode, titanium oxide fine particles were coated onto an FTO (fluorine-doped tin oxide) transparent electrode, and thereafter heating was carried out at 500° C. for one hour. Thereafter, a dye having a structure of FIG. 21C was coated onto the surface, followed by drying to obtain an anode. FIG. 21A shows a schematic view of anode fabrication, and FIG. 21B shows a photograph of the anode after fabrication.

Figure 21D:
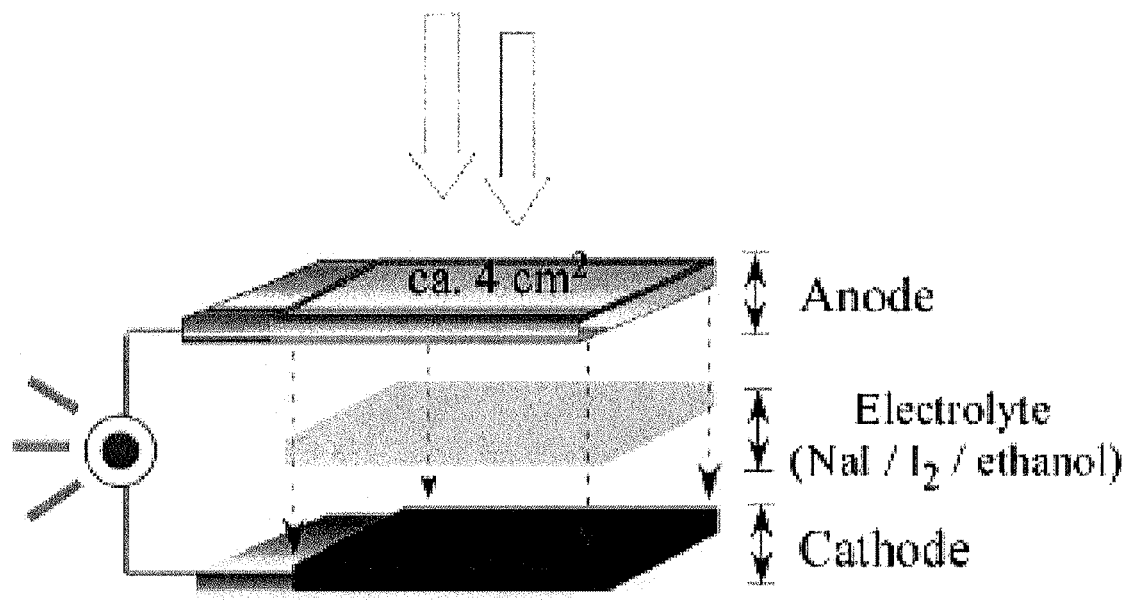
FIG. 21D is a schematic view of a dye-sensitized solar cell.
Figure 21E:
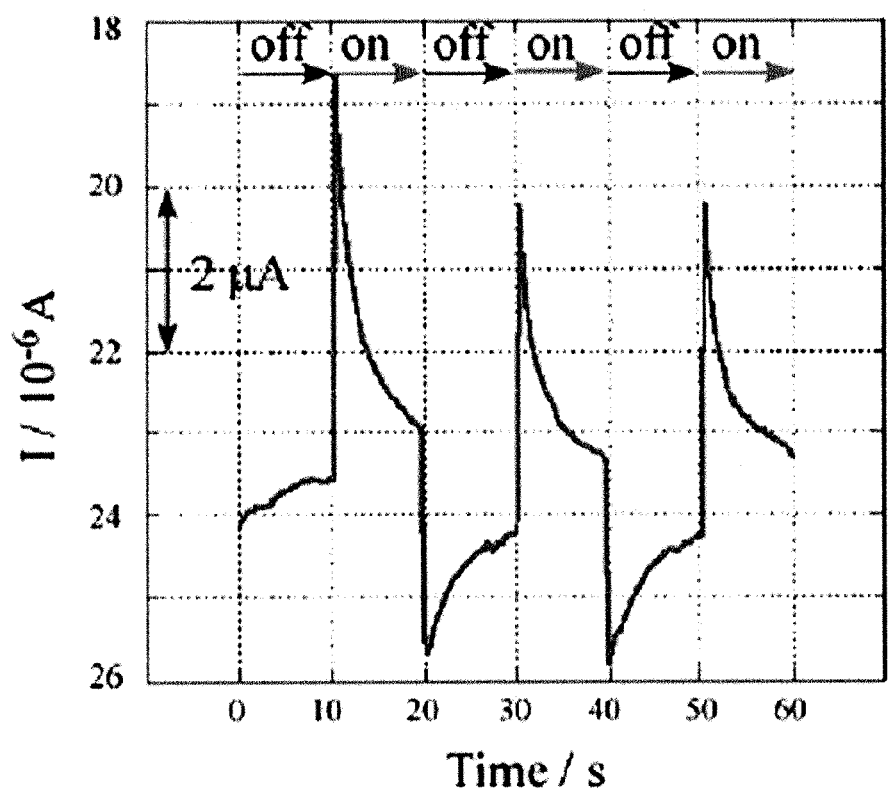
FIG. 21E is a graph showing an optical response in the dye-sensitized solar cell using the CNT composite electrode of the present invention.

Subsequently, a cell having a construction of FIG. 21D was fabricated and irradiated with light (white diode light), whereby generation of a photoelectric current by light irradiation was confirmed as shown in FIG. 21E.

(4-3. Evaluation as Oxygen Electrode for Biofuel Cell)

With use of laccase (Lac) which is useful as an oxygen reduction electrode for a biofuel cell, influence of the CNT interface state and enzyme adsorption amount exerted on the direct electron transfer reaction of an enzyme on the CNTs was studied.

The CNT composite electrode 1 was immersed in a 5 mM of a Lac/phosphoric acid solution (pH 5) to adsorb and immobilize Lac onto the electrode, so as to form a Lac-modified CNT composite electrode 1 (non-oxidized type).

Separately from this, the CNT composite electrode 1 was subjected to electric potential sweeping (0 to 1.2 V vs. Ag/Ag/Cl) for five times in a phosphate buffer solution of pH 7 to perform electrochemical oxidation treatment of the CNTs contained in the electrode, so as to obtain a CNT composite electrode of oxidized type. Here, the G/D ratio of the oxidized type CNT composite electrode D obtained by Raman spectrometry was about 15.

Subsequently, the oxidized CNT composite electrode was immersed in a 5 mM of a Lac/phosphoric acid solution (pH 5) to adsorb and immobilize Lac onto the electrode, so as to form a Lac-modified CNT composite electrode 2 (oxidized type).

Figure 22:
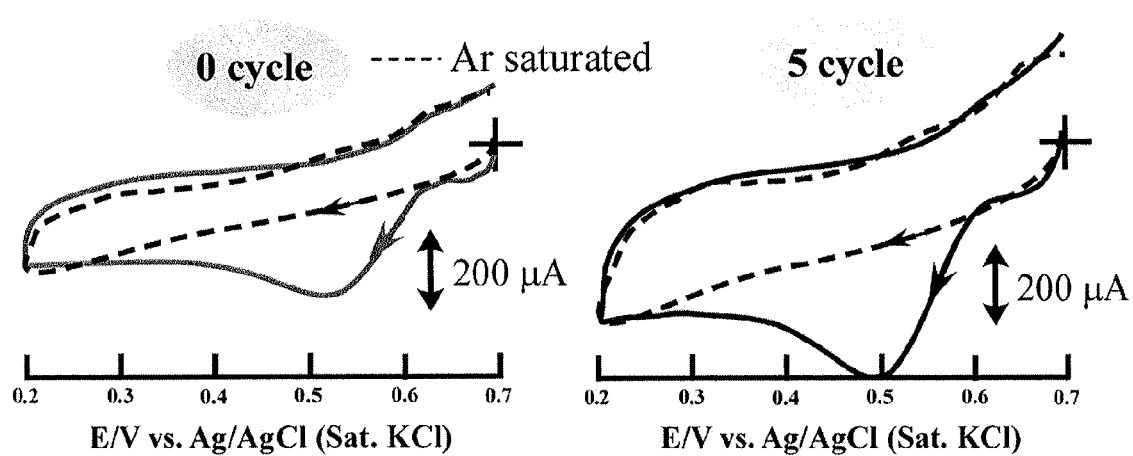
FIG. 22 shows a result of evaluating an enzyme electrode reaction by performing cyclic voltammetry (CV) using Lac-modified CNT composite electrodes 1 and 2.

With respect to the Lac-modified CNT composite electrodes 1 and 2, cyclic voltammetry (CV) was carried out under the following conditions to evaluate the enzyme electrode reaction. The results are shown in FIG. 22.

When CV measurement was carried out using the Lac-modified CNT composite electrodes 1 and 2, the catalytic reduction electric current of oxygen based on the direct electron transfer reaction between Lac and CNT was observed starting from 0.6 V onwards for both of the electrodes.

In particular, in the Lac-modified CNT composite electrode 2 of oxidized type, the largest catalytic reduction electric current of oxygen was observed. This difference in the catalytic electric current value seems to be due to the difference in the enzyme modification amount or the adsorption orientation.

(4-4. Evaluation as Biofuel Cell)

As a cathode, the Lac-modified CNT composite electrode 2 (oxidized type) described above was used.

As an anode, single-walled carbon nanotubes (having a length of 2 cm) were synthesized on a gold wire (having a diameter of 0.8 mm) by a fabrication method that accords to the aforementioned method of fabricating the CNT composite electrode 1. This CNT composite electrode was immersed in a solution of fructose dehydrogenase (FDH) for a predetermined period of time and used as the anode.

Figure 23:
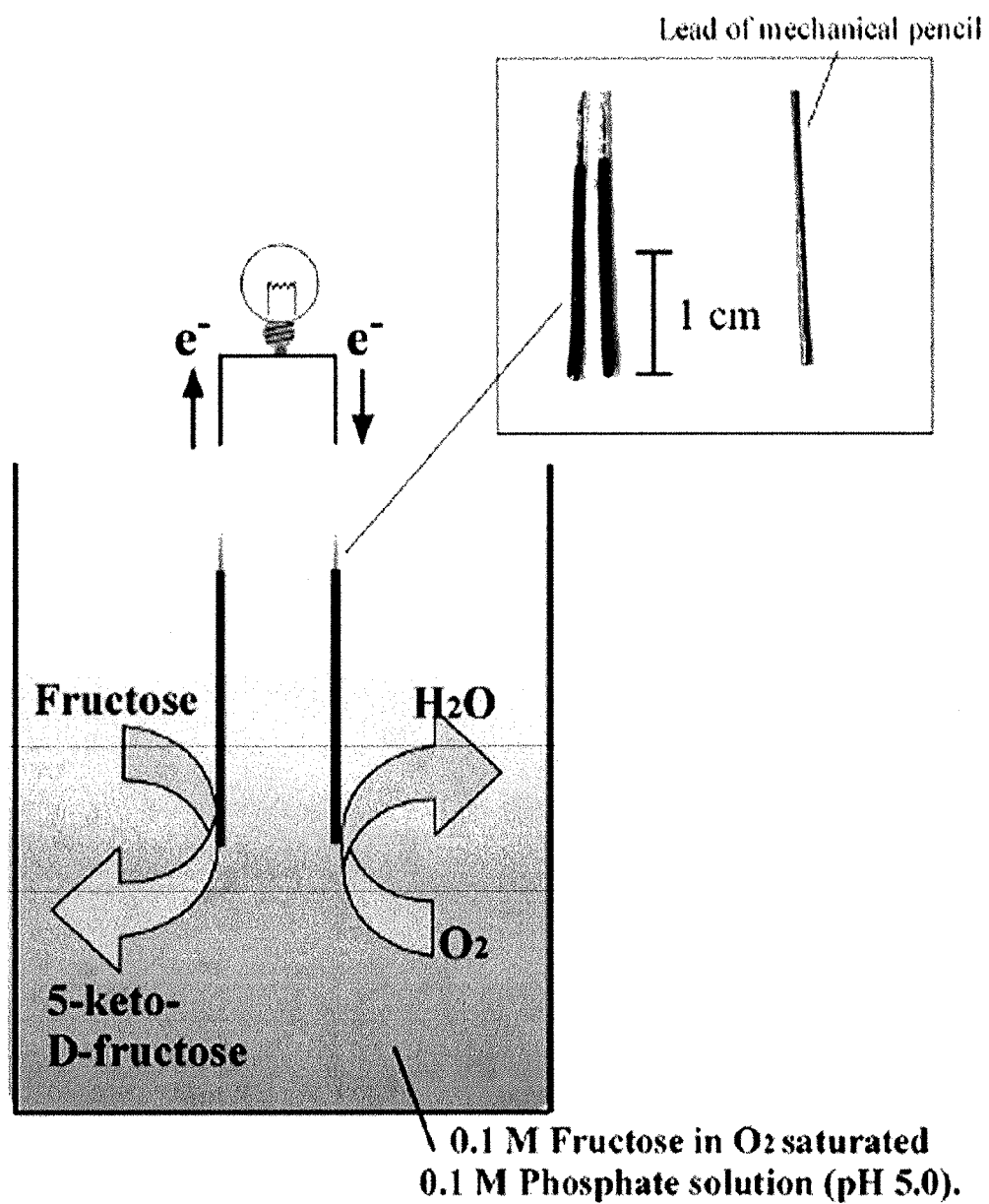
FIG. 23 is a schematic view of a biofuel cell using the CNT composite electrode of the present invention.

The anode and cathode were immersed in a phosphoric acid solution (pH 5, 0.1 M) of 0.1 M fructose saturated with oxygen in a beaker of 100 mL, and a electrical output was measured at room temperature (about 20° C.). A separator that separates the anode from the cathode needs not be used at all. FIG. 23 shows a conceptual view of a cell. As cell characteristics, open-circuit potential: 0.78 V, maximum electric current density: $0.6$ $mA \cdot cm^{-2}$, and maximum electric power: $0.2$ $mW \cdot cm^{-2}$ were confirmed.

(4-5. Evaluation as Thermoelectric Power-Generating Device)

(Fabrication of CNT Composite Electrode 8)

First, cobalt(II) acetate•tetrahydrate and molybdenum acetate were dissolved in 10 mL of ethanol so as to attain 10 wt % and 1.4 wt %, respectively. Subsequently, 5 g of zeolite was added as porous oxide particles and mixed to obtain a catalyst coating liquid for generating CNTs in a slurry form.

As an electrode substrate, a Cu mesh ((The Nilaco Corporation), 100 mesh, thickness of 0.11×100×100 mm) was used, and the Cu mesh was dip-coated with the produced catalyst coating liquid.

Subsequently, the Cu mesh on which the catalyst coating liquid had been applied was put into a CVD apparatus having a construction shown in FIG. 2, and the temperature was raised to 850° C. at a temperature raising speed of about 40° C./min in Ar atmosphere. Here, in this temperature raising step, the volatile components such as ethanol are removed, and zeolite which is a porous oxide material closely adheres to the Cu mesh.

Subsequently, hydrogen was passed at 850° C. for 10 minutes to perform a reduction treatment, thereby to reduce the metal component contained in the catalyst coating liquid.

Subsequently, after the reduction was carried out, mixture gas of hydrogen/ethanol at a volume ratio of 1/2 was passed at 850° C. for 10 minutes to obtain a CNT composite electrode 8. The thickness of the obtained CNT composite electrode 8 was about 0.15 mm.

(Production of Thermoelectric Power-Generating Device)

On one surface of a commercially available Peltier element, a thermally conductive two-sided seal (manufactured by Sumitomo 3M, thickness of about 0.1 mm) was bonded, and the CNT composite electrode 8 that had been cut into 15.1×15.1 mm was bonded thereon to obtain a thermoelectric power-generating device which is Example 1.

(Evaluation)

First, a thick cardboard was cut out into a shape of the thermoelectric power-generating device (shape of the Peltier element), and an aluminum foil for heat dissipation was bonded on the peripheries of the opened window. Subsequently, the thermoelectric power-generating device was fitted into the opened window. Here, a tape, a glue, or the like was not used for fixation of the thermoelectric power-generating device to the cardboard.

Subsequently, as shown by a schematic view of FIG. 24, the cardboard to which the thermoelectric power-generating device had been fitted was placed under a desk lamp serving as a heat source. The desk lamp was fixed so that the electric lamp bulb surface would come to a position of about 10 cm vertically from the thermoelectric power-generating device. The electric lamp bulb in the desk lamp was TOSHIBA 110 V, 40 W, P45 (shape: reflection lamp) and, as the desk lamp, 100 V, 40 W 40 W E17 reflection lamp OHM ELECTRIC INC. 04-6282 was used.

Subsequently, the two surfaces of the thermoelectric power-generating device were connected to an electric current measuring avometer, and the thermoelectric power-generating device was heated and left to stand for cooling by turning the switch of the desk lamp on and off, so as to measure the electric current value.

In addition, as Comparative Example 1, a thermoelectric power-generating device of Comparative Example 1, in which the commercially available Peltier element was used as it was, was evaluated by a procedure similar to that of Example 1.

In addition, as Comparative Example 2, a thermoelectric power-generating device of comparative example in which the thermally conductive two-sided seal had been bonded to the commercially available Peltier element was evaluated by a procedure similar to that of Example 1.

In addition, as Comparative Example 3, a thermoelectric power-generating device in which the thermally conductive two-sided seal had been bonded to the commercially available Peltier element and the Cu mesh had been bonded thereon was evaluated by a procedure similar to that of Example 1.

Figure 25:
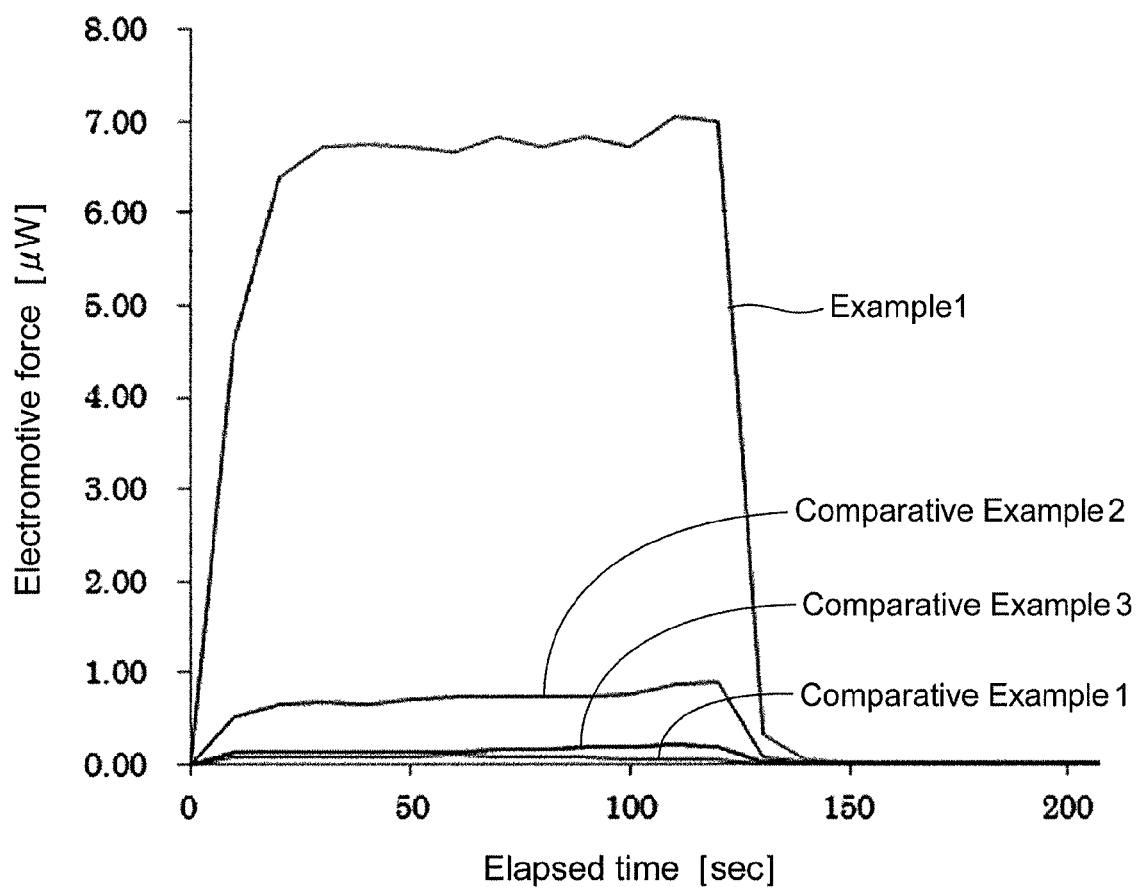
FIG. 25 shows a result of evaluating thermoelectric power-generating devices of examples and comparative examples.

FIG. 25 shows a result of evaluation of the thermoelectric power-generating devices of Example 1 and Comparative Examples 1 to 3.

It has been shown that, in the devices of the Peltier element and the Peltier element/thermally conductive two-sided seal/copper mesh, little thermoelectric power generation occurred, and little temperature difference was generated between the surface of the Peltier element irradiated with the lamp and the opposite surface thereof. It has been found out that, in the device of the Peltier element/thermally conductive two-sided seal, the thermally conductive two-sided seal absorbed the heat and light from the light source, and the Peltier element surface thereof was heated. Further, in the device of the Peltier element/thermally conductive two-sided seal/CNT composite electrode 8, thermoelectric power generation occurred to an extent of 7 times or more as compared with the device of the Peltier element/thermally conductive two-sided seal. Because carbon nanotubes absorb light in a wide range from visible light region to near infrared region to generate heat and the thermal conductivity of the carbon nanotubes is equivalent to or more than that of diamond, it has been found out that, in the device of the Peltier element/thermally conductive two-sided seal/CNT composite electrode 8, heat and light from the light source were efficiently absorbed, and also the heat was transferred efficiently to the Peltier element surface.

(4-6. Electrochemical End-Opening Treatment of CNT)

By a method similar to the above, four CNT composite electrodes 1 (substrate electrode: Au wire, porous oxide material: zeolite) were produced.

To the produced CNT composite electrodes 1, a predetermined electric potential shown below was applied for 30 minutes using a three-electrode type cell having a construction as follows, whereby the CNTs were electrochemically decomposed by oxidation to obtain CNT composite electrodes a, b, c, and d containing CNTs with an open end. Here, with respect to the CNT composite electrode a in which the applied electric potential was 0 V, substantially no electrochemical end-opening treatment was carried out.

Before application of the electric potential, bubbling was carried out with high-purity argon (Assay: 99.99% or more) for 30 minutes or more to remove the dissolved oxygen. At the time of electric potential application, high-purity argon was allowed to flow within the cell, and the electric potential application was carried out in argon atmosphere.

<Cell Construction>

W.E.: CNT composite electrode 1

C.E.: Pt wire

R.E.: Ag/AgCl electrolytic solution: 0.1 M phosphate buffer solution (pH 7)

<Applied Electric Potential>

CNT composite electrode a: 0 V (vs. Ag/AgCl)

CNT composite electrode b: 0.8 V (vs. Ag/AgCl)

CNT composite electrode c: 1.0 V (vs. Ag/AgCl)

CNT composite electrode d: 1.3 V (vs. Ag/AgCl)

(4-7. Modification of CNT with β-Carotene)

By using β-carotene which is one kind of carotenoids as a to-be-incorporated modifying substance, incorporation modification with β-carotene was carried out on the CNT composite electrodes a to d by a method shown below.

Figure 26:
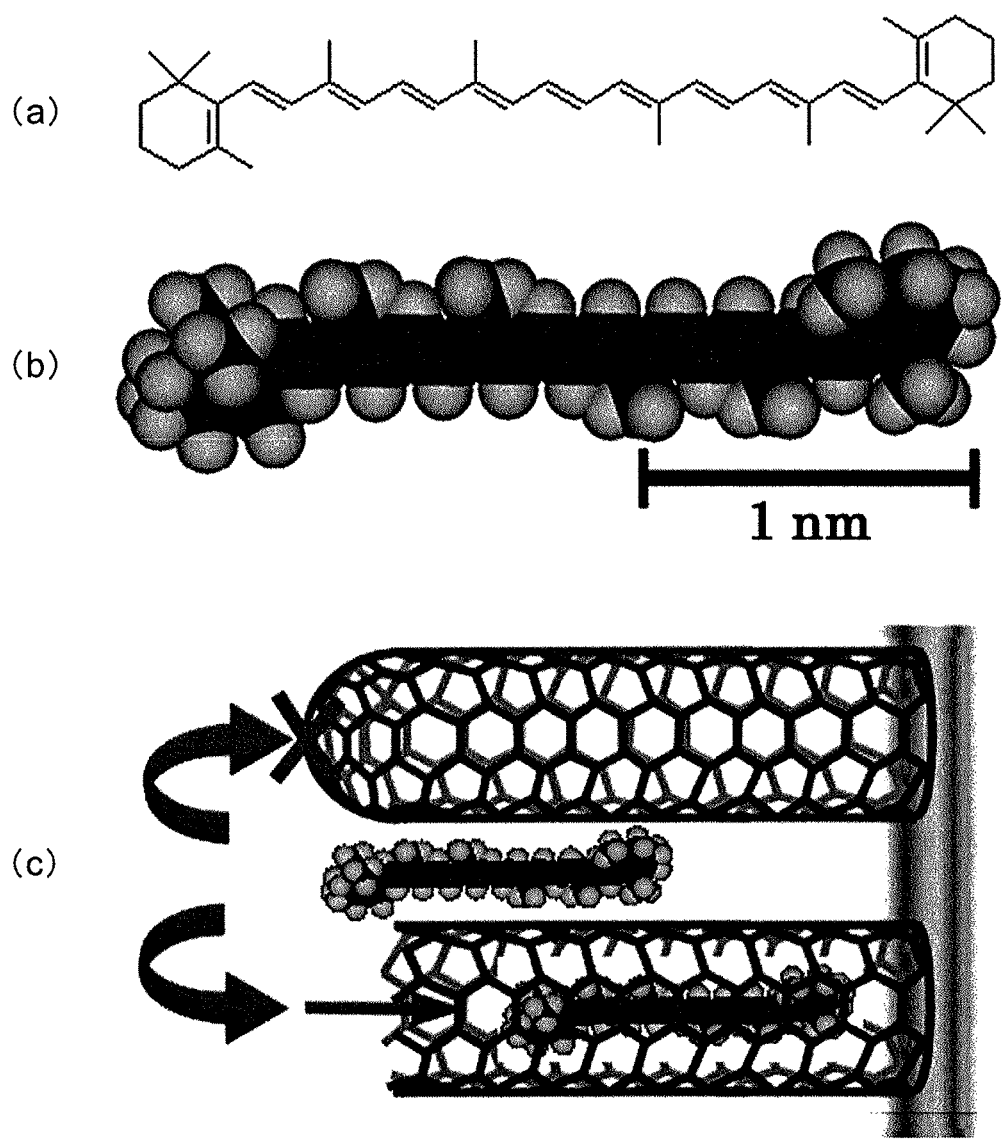
FIG. 26(a) shows a chemical structural formula of β-carotene.
FIG. 26(b) is a schematic view of β-carotene.
FIG. 26(c) is a schematic view showing how β-carotene is incorporated into a CNT composite electrode subjected to an open end treatment.

FIG. 26(*a*) shows a chemical structural formula of β-carotene; FIG. 26(*b*) shows a schematic view of β-carotene; and FIG. 26(*c*) shows a schematic view showing how β-carotene is incorporated into the CNT composite electrode subjected to an end-opening treatment.

(Production of β-Carotene-Modified CNT Composite Electrode (β-Car/CNT Composite Electrode))

Modification of the CNT composite electrode a with β-carotene was carried out by the following procedure.

First, on a hexane solution containing 2 μM β-carotene, bubbling was carried out with high-purity argon (Assay: 99.99% or more) for 30 minutes or more to remove the dissolved oxygen. Thereafter, the CNT composite electrode a was immersed, and refluxing with heating was carried out at 70° C. for 10 hours. At the time of heating, high-purity argon was continuously allowed to bubble in the hexane solution of β-carotene. After the heating, the CNT composite electrode a was taken out from a three-neck flask and washed with tetrahydrofuran (THF) to obtain a β-carotene-modified CNT composite electrode a.

Here, the washing operation was carried out by adding the CNT composite electrode a and 3 mL of THF into a reagent bottle (5 mL) and stirring them for 10 minutes with a magnetic stirrer. The washing operation was carried out for three times by exchanging THF.

(Production of β-Carotene-Modified CNT Composite Electrodes b, c, and d)

β-Carotene-modified CNT composite electrodes b, c, and d were obtained by a method similar to the method for producing the β-carotene-modified CNT composite electrode a except that the CNT composite electrodes b, c, and d were used instead of the CNT composite electrode a.

(Evaluation: Raman Spectrometry)

For CNT evaluation of the CNT composite electrode, a laser Raman spectrometry apparatus (LabRAM HR-800) manufactured by HORIBA LTD. was used (measurement conditions: laser wavelength: 514.5 nm, exposure time: 60 seconds, cumulated number: 3 times).

The results of Raman spectrometry of the β-carotene-modified CNT composite electrodes a to d are shown in FIGS. 27(b) to 27(e). Here, for the sake of reference, the spectrum of the CNT composite electrode not modified with β-carotene yet (CNT composite electrode 1) (FIG. 27(a)) and the spectrum of β-carotene alone (FIG. 27(f)) are shown together.

The β-carotene-modified CNT composite electrode c treated with an applied electric potential of 1.0 V has Raman peaks of 1157 cm$^{-1}$ and 1525 cm$^{-1}$ derived from β-carotene in addition to the Raman peak derived from the CNT not modified with β-carotene yet (see FIG. 27(a)). In the spectrum of β-carotene alone (FIG. 27(f)), the peaks are seen at 1152 cm$^{-1}$ and 1524 cm$^{-1}$; however, with respect to the Raman peaks derived from β-carotene in the β-carotene-modified CNT composite electrode c, a peak shift was observed. This seems to be caused by the electric charge transfer between the incorporated β-carotene and the CNTs, showing that the β-carotene is incorporated.

In the β-carotene-modified CNT composite electrode b treated by 0.8 V application, the peak intensity derived from β-carotene is weak, so that it seems that the end opening of the CNTs is insufficient, and the amount of incorporation of β-carotene is decreased. On the other hand, in the β-carotene-modified CNT composite electrode a that had not been subjected to an end-opening treatment, fine peaks were observed in the vicinity of 1159 cm$^{-1}$ and 1520 cm$^{-1}$. Because the CNTs in the composite electrode do not have an open end, this seems to be due to the fact that a slight amount of β-carotene entered between the bundles of the CNTs. Further, it has been found out that an excessive electric potential application treatment is not suitable for β-carotene incorporation. For example, in the CNT composite electrode d treated by 1.3 V application, the peak intensity of the D-band derived from a CNT defect structure was large, so that it has been determined that not only the terminal end but also the side surface was oxidized. In this CNT composite electrode d, the peak derived from β-carotene was little observed.

From the above, it has been shown that there is an optimal electric potential for an electrochemical CNT end-opening treatment for modification with β-carotene by incorporation. It has been found out that, for the electrochemical CNT oxidation end-opening treatment under the conditions with an electrolyte solution of pH 7, an electric potential of 0.9 to 1.1 V is suitable.

(Evaluation: Cyclic Voltammetry)<
Measurement Conditions>

With use of a three-electrode type cell having a construction as follows, bubbling was carried out with high-purity argon (Assay: 99.99% or more) for 30 minutes or more to remove the dissolved oxygen before the cyclic voltammogram measurement. At the time of measurement, high-purity argon was allowed to flow within the cell, and the measurement was carried out in argon atmosphere.

<Cell Construction>

W.E.: CNT composite electrode c modified by β-carotene incorporation or CNT composite electrode 1

C.E.: Pt wire

R.E.: Ag/AgCl (saturated KCl)

electrolytic solution: 0.1 M phosphate buffer solution (pH 7)

Figure 28:
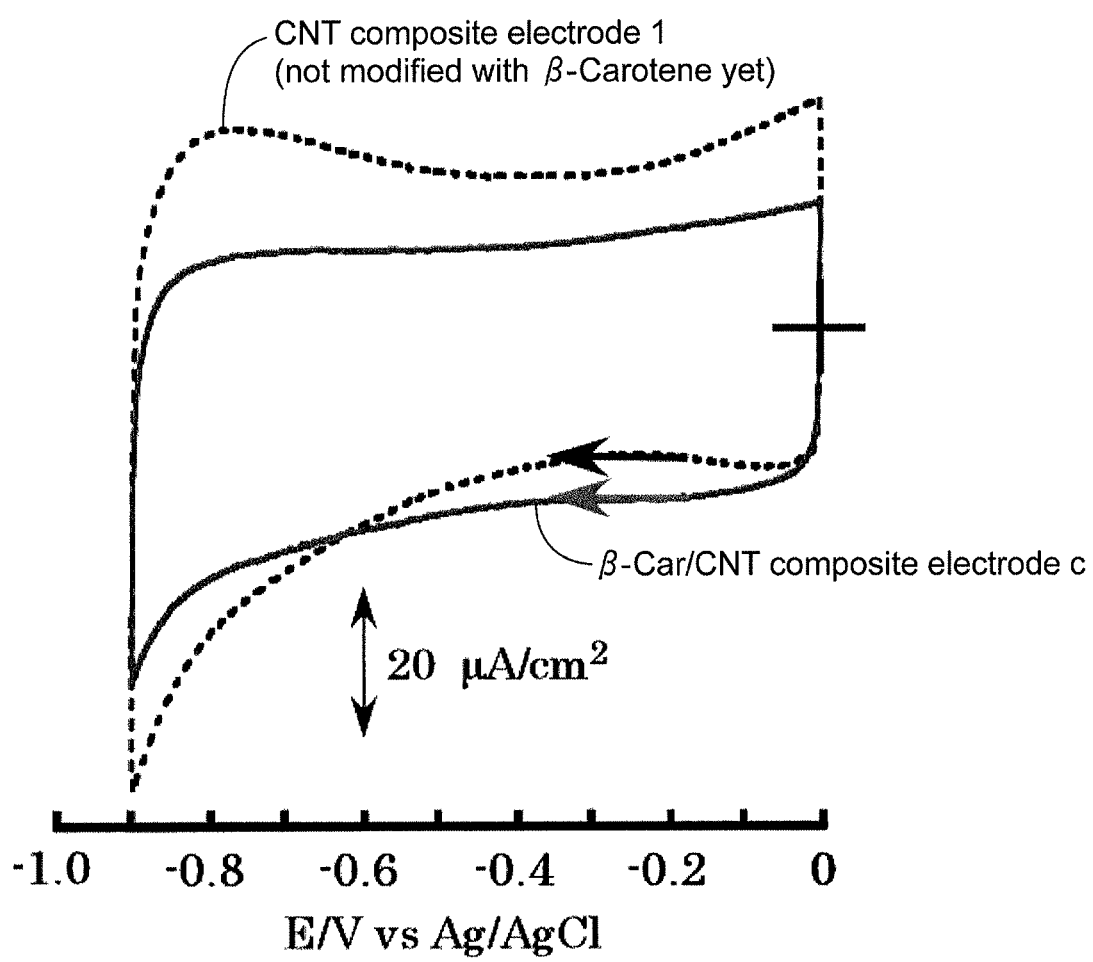
FIG. 28 shows a result of CV measurement of the β-carotene-modified CNT composite electrode c and a modified CNT composite electrode not modified with β-carotene yet (CNT composite electrode 1).

FIG. 28 shows a cyclic voltammogram of the CNT composite electrode c modified with β-carotene by incorporation and the CNT composite electrode 1 that has not been subjected to an incorporation treatment. In generally synthesized single-walled CNTs, metallic ones and semiconductive ones are mixedly present. It has been separately confirmed by Raman spectroscopy that the CNT composite electrodes of the present invention also have been fabricated in such a manner that metallic CNTs and semiconductive CNTs are mixedly present. In the ordinary CNT composite electrode 1 that has not been subjected to an incorporation treatment, doping or dedoping of electrons to the semiconductive CNTs occurs by electric potential sweeping application in the voltammogram, so that the cyclic voltammogram is known to have a shape of a butterfly with spread wings (butterfly type). Under the present conditions also, the voltammogram was a butterfly-type voltammogram having a recess at −0.6 to −0.2 V (vs. Ag/AgCl). On the other hand, in the CNT composite electrode c modified with β-carotene by incorporation, the voltammogram was not a butterfly-type voltammogram. This seems to be due to the fact that the carriers in the incorporated β-carotene moved to the semiconductive CNTs of the CNT composite electrode c to change the semiconductive CNTs into metallic ones.

INDUSTRIAL APPLICABILITY

According to the present invention, a carbon nanotube composite electrode having carbon nanotubes firmly fixed to an electrode substrate and having a wide effective electrode area is provided.

The carbon nanotube composite electrode is excellent in mechanical strength and electric conductivity; in particular, no exfoliation of CNTs from the electrode occurs in the solution; further, the CNTs are moderately dispersed on the electrode; and the transfer of substances between the inside of the CNT layer in the solution and the solution layer on the outside thereof is smooth. Therefore, the carbon nanotube composite electrode can be applied suitably for use as an electrode in biosensors, biobatteries, fuel batteries, capacitors, electrochemical detection devices for analysis, neural network models, solar batteries, and the like.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims. No. 2011-108659 filed on May 13, 2011.

The entire disclosure of Japanese Patent Application including specification, claims, drawings and summary is incorporated herein by reference in its entirety.

DRAWINGS

Figure 24:
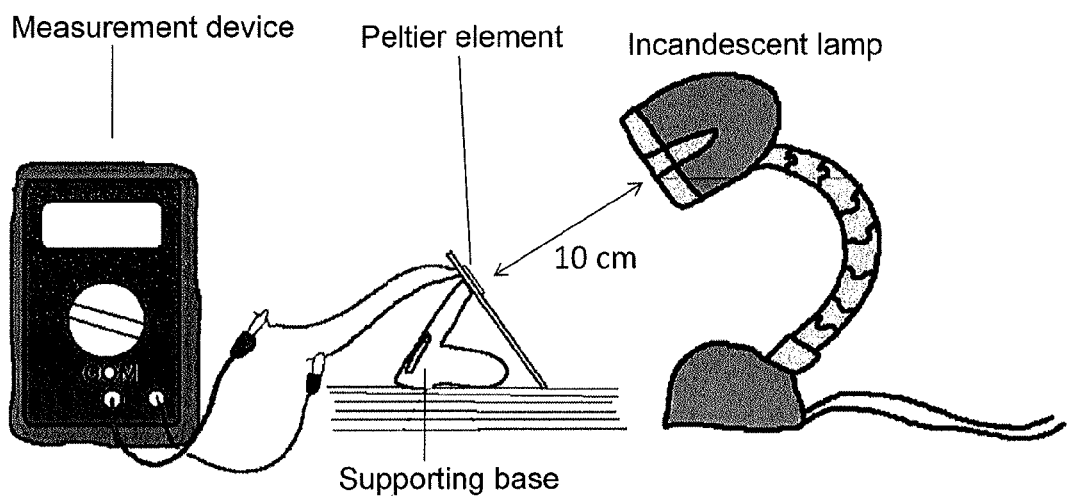
FIG. 24 is a schematic view of a method for evaluating a thermoelectric power-generating device.
Figure 27:
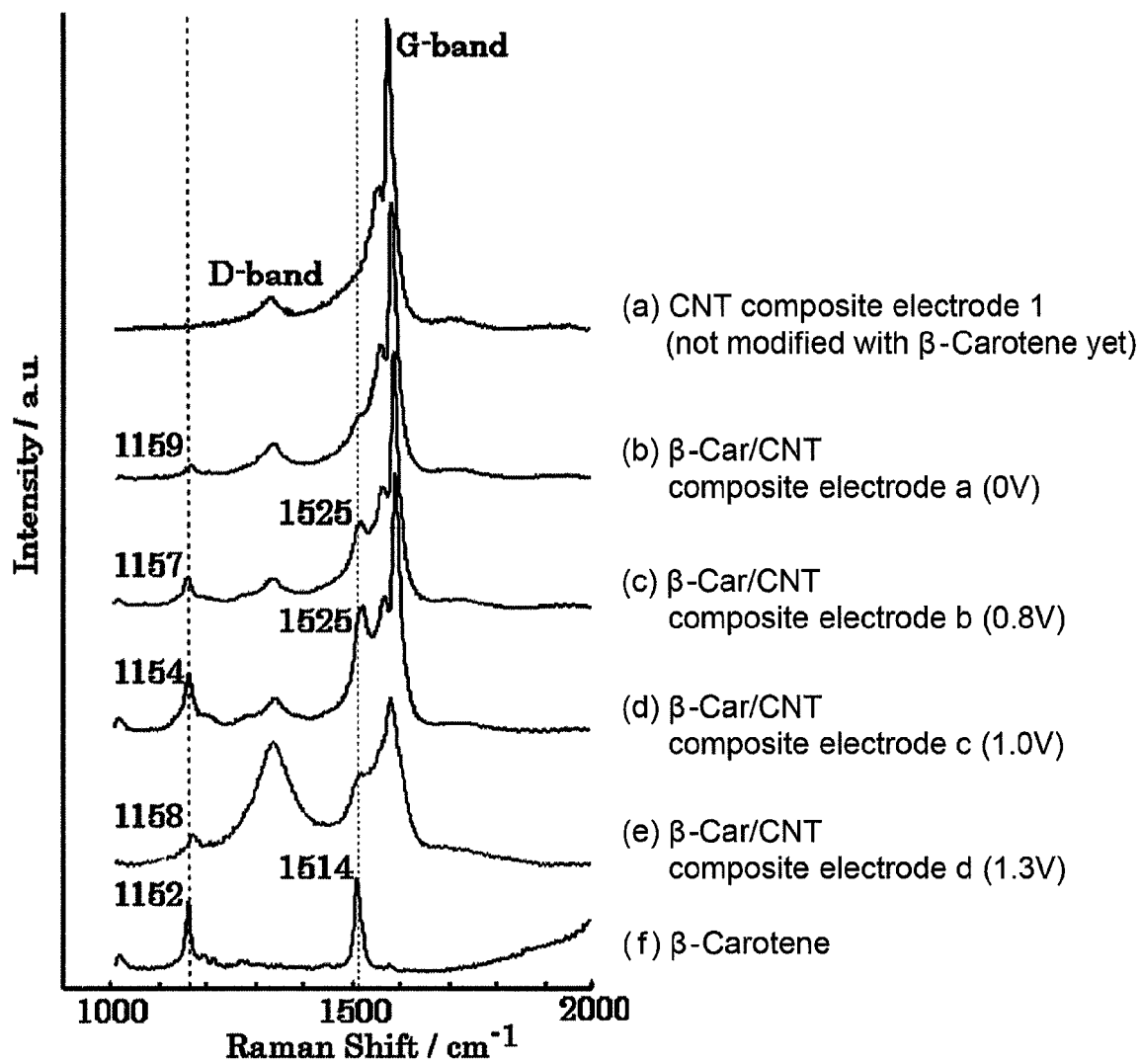
FIG. 27 shows a result of Raman spectrometry of a β-carotene-modified CNT composite electrode, where the respective spectra represent (a) a CNT composite electrode not modified with β-carotene yet, (b) a β-carotene-modified CNT composite electrode a, (c) a β-carotene-modified CNT composite electrode b, (d) a β-carotene-modified CNT composite electrode c, (e) a β-carotene-modified CNT composite electrode d, and (f) β-carotene alone.

FIG. 1
(1) Surface layer
(2) Electrode substrate
(3) Porous oxide material
FIG. 5
(1) Porous oxide material
(2) Surface layer
(3) Electrode substrate
FIG. 6
(1) Porous oxide material
(2) Electrode substrate
FIG. 13
(1) (A) Cycle oxidation for 5 times
(2) (B) Cycle oxidation for 10 times
(3) (C) Cycle oxidation lot 20 times
FIG. 20
(1) With oxygen degassed
 With oxygen aerated
(2) With no glucose
 With 50 mM glucose
FIG. 21
(1) Dye
FIG. 24
(1) Measurement device
(2) Peltier element
(3) Incandescent lamp
(4) Supporting base
FIG. 25
(5) Electromotive force
(6) Example 1
(7) Comparative Example 2
(8) Elapsed time
FIG. 27
(1)
(a) CNT composite electrode 1 (not modified with β-Carotene yet)
(b) β-Car/CNT composite electrode a (0 V)
FIG. 28
(1) CNT composite electrode 1 (not modified with β-Carotene yet)
(2) β-Car/CNT composite electrode c

The invention claimed is:

1. A carbon nanotube composite electrode comprising a surface layer containing a porous oxide material and carbon nanotubes on a surface of an electrode substrate, wherein the carbon nanotubes are generated from the porous oxide material, and at least some of the carbon nanotubes are electrically connected to the electrode substrate, wherein the carbon nanotubes contain carbon nanotubes generated from pores of the porous oxide material, and wherein the porous oxide material is zeolite.

2. The carbon nanotube composite electrode according to claim 1, wherein the electrode substrate is an electrode substrate made of gold (Au) or an electrode substrate plated with gold (Au).

3. The carbon nanotube composite electrode according to claim 1, wherein some of the carbon nanotubes generated from the porous oxide material are partially embedded in the surface of the electrode substrate.

4. The carbon nanotube composite electrode according to claim 1, wherein the carbon nanotubes are carbon nanotubes generated from metal catalyst fine particles supported on the porous oxide material.

5. The carbon nanotube composite electrode according to claim 4, wherein the amount of the supported metal fine particles is 0.1 parts by weight or more and 10 parts by weight or less relative to 100 parts by weight of the porous oxide material.

6. The carbon nanotube composite electrode according to claim 1, wherein 70% or more of the total number of the carbon nanotubes are single-walled carbon nanotubes.

7. The carbon nanotube composite electrode according to claim 1, wherein the carbon nanotubes are non-oxidized type carbon nanotubes.

8. The carbon nanotube composite electrode according to claim 1, wherein a metal and/or a semiconductor are firmly immobilized on a wall surface of the carbon nanotubes.

9. The carbon nanotube composite electrode according to claim 8, wherein the metal and/or the semiconductor are fine particles having an average particle size of 100 nm or less.

10. The carbon nanotube composite electrode according to claim 9, wherein 80% or more of the total number of the fine particles have a particle size within a range of 0.5 nm or more and 5 nm or less.

11. The carbon nanotube composite electrode according to claim 1, wherein a wall surface of the carbon nanotubes is covered with a surface-modifying substance.

12. The carbon nanotube composite electrode according to claim 11, wherein the surface-modifying substance is a surfactant.

13. The carbon nanotube composite electrode according to claim 1, wherein a tip of at least some of the carbon nanotubes is open-ended.

14. The carbon nanotube composite electrode according to claim 13, which is electrochemically open-ended.

15. The carbon nanotube composite electrode according to claim 13, wherein the open-ended carbon nanotubes incorporate an incorporated modifying substance.

16. The carbon nanotube composite electrode according to claim 15, wherein the incorporated modifying substance is carotenoid.

* * * * *